United States Patent
Duhren-Von Minden

(10) Patent No.: US 11,981,735 B2
(45) Date of Patent: *May 14, 2024

(54) ANTIBODIES TARGETING THE B-CELL RECEPTOR OF CHRONIC LYMPHOCYTIC LEUKEMIA AND USES THEREOF

(71) Applicant: AVA Lifescience GmbH, Denzlingen (DE)

(72) Inventor: Marcus Duhren-Von Minden, Mullheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/161,070

(22) Filed: Jan. 29, 2023

(65) Prior Publication Data

US 2023/0272073 A1 Aug. 31, 2023

(30) Foreign Application Priority Data

Feb. 10, 2022 (EP) .................................... 22156205

(51) Int. Cl.
 *C07K 16/28* (2006.01)
 *A61P 35/00* (2006.01)
 *C07K 16/46* (2006.01)

(52) U.S. Cl.
 CPC .......... *C07K 16/2803* (2013.01); *A61P 35/00* (2018.01); *C07K 2317/24* (2013.01)

(58) Field of Classification Search
 CPC .......................... C07K 16/30; A61K 39/39558
 See application file for complete search history.

(56) References Cited

U.S. PATENT DOCUMENTS

| | | | |
|---|---|---|---|
| 2003/0148321 A1* | 8/2003 | Pecker | G01N 33/57426 435/6.16 |
| 2007/0258979 A1* | 11/2007 | Ashman | A61P 33/12 435/328 |
| 2008/0280297 A1* | 11/2008 | Dalla-Favera | G01N 33/57426 435/6.16 |
| 2011/0190157 A1* | 8/2011 | Kipps | C12Q 1/6809 506/17 |
| 2020/0199225 A1 | 6/2020 | Birsner et al. | |
| 2020/0209246 A1 | 7/2020 | Birsner et al. | |

FOREIGN PATENT DOCUMENTS

| | | |
|---|---|---|
| JP | 2020526590 | 8/2020 |
| JP | 2020527727 | 9/2020 |
| WO | 2019008128 | 1/2019 |
| WO | 2019008129 A1 | 1/2019 |
| WO | 2020127827 A1 | 6/2020 |
| WO | 2020221466 A1 | 11/2020 |

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Baxevanis (Expert Opinion: Drug Discovery, vol. 3, No. 4, p. 441-452, 2008) (Year: 2008).*
Maity Palash C. et al: "IGLV3-21*01 is an inherited risk factor for CLL through the acquisition of a single-point mutation enabling autonomous BCR signaling," Proceedings of the National Academy of Sciences, vol. 117, No. 8, Feb. 11, 2020 (Feb. 11, 2020), pp. 4320-4327, XP055939305, ISSN: 0027-8424, DOI: 10.1073/pnas.1913810117.
Maity Palash C. et al.: "IGLV3-21*01 is an inherited risk factor for CLL through the acquisition of a single-point mutation enabling autonomous BCR signaling—supporting information," Proceedings of the National Academy of Sciences, vol. 117, No. 8, Feb. 11, 2020 (Feb. 11, 2020), pp. 4320-4327, XP055939309, ISSN: 0027-8424, DOI: 10.1073/pnas.1913810117, table on p. 4 suppl. info.
Patel Krish et al: "Current and future treatment strategies in chronic lymphocytic leukemia," Journal of Hematology & Oncology, vol. 14, No. 1, Apr. 26, 2021 (Apr. 26, 2021), XP055939369, DOI: 10.1186/s13045-021-01054-w.
James Torchia et al: "Targeting lymphoma with precision using semisynthetic anti-idiotype peptibodies," Proceedings of .the National Academy of Sciences, vol. 113, No. 19, Apr. 25, 2016 (Apr. 25, 2016), pp. 5376-5381, XP055565565, ISSN: 0027-8424, DOI: 10.1073/pnas.1603335113.
Macarron Palacios Arturo et al.: "Specific Targeting of Lymphoma Cells Using Semisynthetic Anti-Idiotype Shark Antibodies", Frontiers in Immunology, vol. 11, Nov. 26, 2020 (Nov. 26, 2020), XP055880182, Lausanne, CH ISSN: 1664-3224, DOI: 10.3389/firnrnu.2020.560244.
Sawalha Yazeed et al.: "Novel treatments in B cell non-Hodgkin's lymphomas," BMJ, Apr. 20, 2022 (Apr. 20, 2022), p. XP055939610, DOI: 10.1136/bmj-2020-063439.
EP 22156205, European Search Report, dated Jul. 7, 2022, EPO, The Hague.

* cited by examiner

*Primary Examiner* — Michael Allen
(74) *Attorney, Agent, or Firm* — SAFFIRE IP; Daren P. Nicholson

(57) ABSTRACT

The present invention provides antibodies for the treatment of chronic lymphocytic leukemia (CLL). These antibodies target the B-cell receptor (BCR) of CLL cells characterised by R110-mutated immunoglobulin lambda variable 3-21 (IGLV3-21$^{R110}$).

The invention also provides nucleic acid sequences encoding the forgoing antibodies, vectors containing the same, pharmaceutical compositions and kits with instructions for use.

12 Claims, 15 Drawing Sheets
Specification includes a Sequence Listing.

Figure 1
Figure 1A
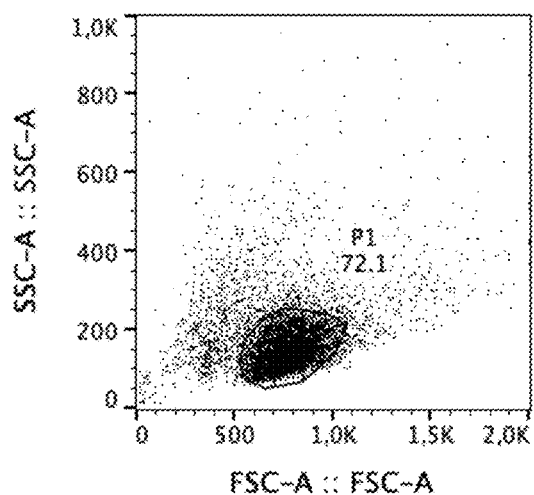
Figure 1B
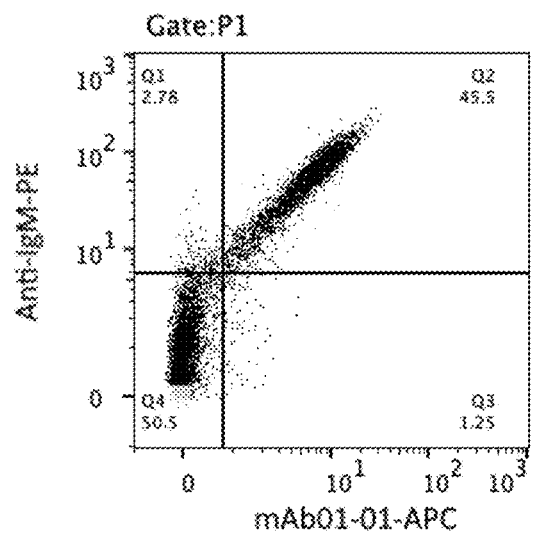
Figure 1C
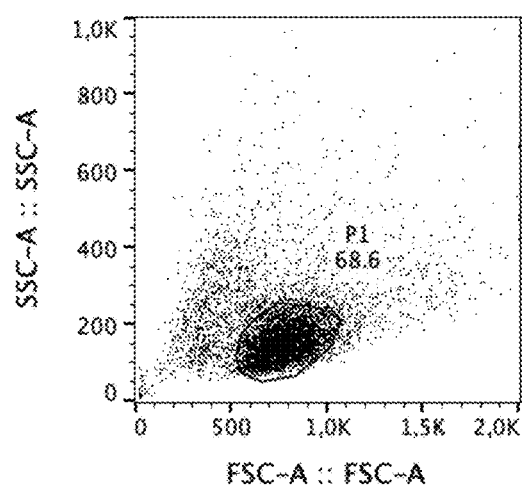
Figure 1D
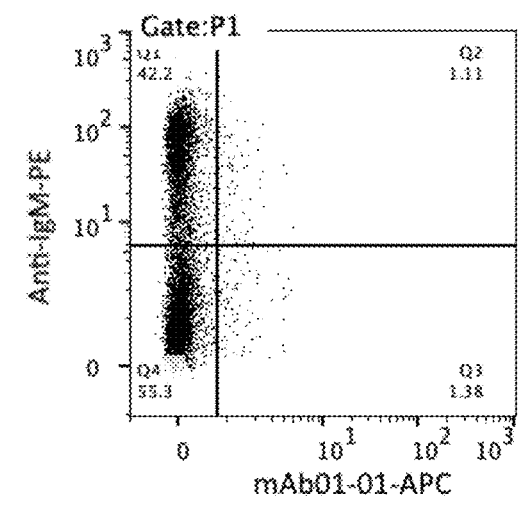

Figure 2
Figure 2A
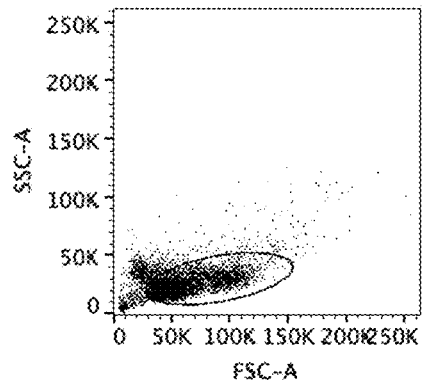
Figure 2B
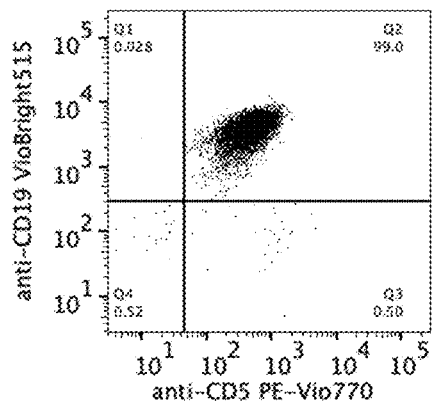
Figure 2C
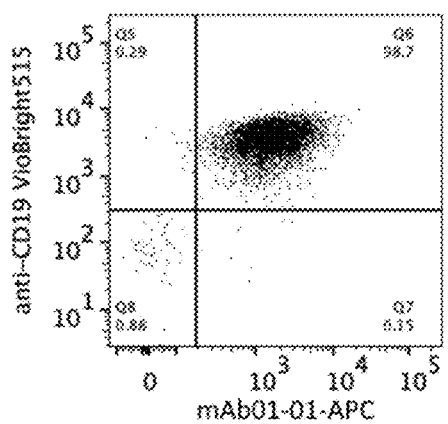
Figure 2D
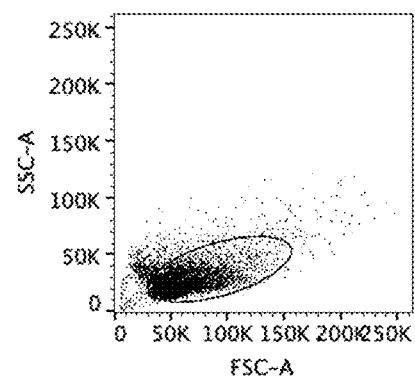
Figure 2E
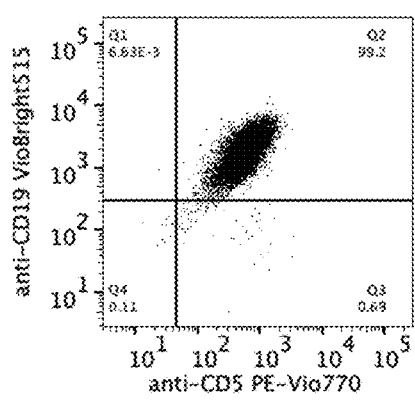
Figure 2F
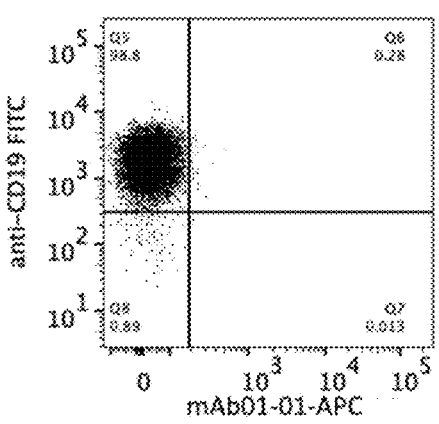

| 1st AB: mAb01-01 | + | - |
| 2nd AB: anti-IgG | + | + |

Spleen — CLL-IgLV3-21^R110

Healthy human tissue samples

Spleen

Skin

Kidney

Heart

Brain

SYELTQPPSVSVAPGKTARITCAGNNIGSKSVHWYQQKPGQAPVLVIYYDSDRPSGI-
PERFSGSNSGNTATLTISRVEAGDEADYYCQVWDSGSDHPWVFGGGTKLTVLR

SEQ ID NO: 53

| AA pos. | 16 | 49 | 50 | 51 | 52 | 110 | |
|---|---|---|---|---|---|---|---|
| | Lys | | Asp | | Asp | | Arg | SEQ ID NO: 53 |
| | Lys | | Tyr | Asp | Ser | Asp | Arg | SEQ ID NO: 53 |

AA pos. = amino acid position in IGLV3-21$^{R110}$

Figure 8:

SEQ ID NO: 1 (polypeptide):
QVQLQQSGPGLVQPSQSLSITCTVSGFSLTSYGIHWVRQSPGKGLEWLGVIWRGGGTDSNA
AFMSRLSITKDNSKSQVFFKMNSLQADDTAIYYCARSRYDEEESMNYWGQGTSVTVSSAKTT
PPSVYPLAPGSAAQTNSMVTLGCLVKGYFPEPVTVTWNSGSLSSGVHTFPAVLQSDLYTLSS
SVTVPSSPRPSETVTCNVAHPASSTKVDKKIVPRDCGCKPCICTVPEVSSVFIFPPKPKDVLTIT
LTPKVTCVVVDISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMNTNGSYFVYSKLNVQKSNWEAGNTFTCSVLHEGLHNHHTEKS
LSHSPGK SEQ ID NO: 2 (polypeptide):
QIVLTQSPASLSASVGETVTITCRASGNIHSYLAWYQQKQGKSPQLLVYNAKTLADGVPSRFS
GSGSGTQYSLKINSLQPEDFGSYYCQHFWNTPPTFGAGTKLELKRADAAPTVSIFPPSSEQLT
SGGASVVCFLNNFYPKDINVKWKIDGSERQNGVLNSWTDQDSKDSTYSMSSTLTLTKDEYER
HNSYTCEATHKTSTSPIVKSFNRNEC SEQ ID NO: 3 (polypeptide):
QVQLQQSGPGLVQPSQSLSITCTVSGFSLTSYGIHWVRQSPGKGLEWLGVIWRGGGTDSNA
AFMSRLSITKDNSKSQVFFKMNSLQADDTAIYYCARSRYDEEESMNYWGQGTSVTVSS SEQ ID NO: 4 (polypeptide):
QIVLTQSPASLSASVGETVTITCRASGNIHSYLAWYQQKQGKSPQLLVYNAKTLADGVPSRFS
GSGSGTQYSLKINSLQPEDFGSYYCQHFWNTPPTFGAGTKLELKR SEQ ID NO: 5 (polypeptide):
GFSLTSYG SEQ ID NO: 6 (polypeptide):
IWRGGGT SEQ ID NO: 7 (polypeptide):
ARSRYDEEESMNY SEQ ID NO: 8 (polypeptide):
GNIHSY SEQ ID NO: 9 (polypeptide):
NAKT SEQ ID NO: 10 (polypeptide):
QHFWNTPPT SEQ ID NO: 11 (polypeptide):
QVQLQQSGPGLVQPSQSLSITCTVSGFSLTSYGIHWVRQSPGKGLEWLGVIWRGGGTDSNA
AFMSRLSITKDNSKSQVFFKMNSLQADDTAIYYCARSRYDEEESMNYWGQGTSVTVSSASTK
GPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEAL
HNHYTQKSLSLSPGK (Fig. 8 continued)

SEQ ID NO: 12 (polypeptide):
QIVLTQSPASLSASVGETVTITCRASGNIHSYLAWYQQKQGKSPQLLVYNAKTLADGVPSRFS
GSGSGTQYSLKINSLQPEDFGSYYCQHFWNTPPTFGAGTKLELKRTVAAPSVFIFPPSDEQLK
SGTASVVCLLNNFYPREAKVQWKVDNALQSGNSQESVTEQDSKDSTYSLSSTLTLSKADYEK
HKVYACEVTHQGLSSPVTKSFNRGEC SEQ ID NO: 13 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGK SEQ ID NO: 14 (polypeptide):
EIVLTQSPSSLSASVGDSVTITCRASGNIHSYLAWYQQKPGKAPKLLIYNAKTLADGVPSRFSG
SGSGTQYTLTISSLQPEDFATYYCQHFWNTPPTFGAGTKLELKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC SEQ ID NO: 15 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSS SEQ ID NO: 16 (polypeptide):
EIVLTQSPSSLSASVGDSVTITCRASGNIHSYLAWYQQKPGKAPKLLIYNAKTLADGVPSRFSG
SGSGTQYTLTISSLQPEDFATYYCQHFWNTPPTFGAGTKLELKR SEQ ID NO: 17 (polypeptide):
QIQLTQSPSFLSASVGDSVTITCRASGNIHSYLAWYQQKPGKAPQLLIYNAKTLADGVPSRFS
GSGSGTEYTLTISSLQPEDFATYYCQHFWNTPPTFGAGTKLELKR SEQ ID NO: 18 (polypeptide):
EIVLTQSPATLSLSPGERATLSCRASGNIHSYLAWYQQKPGQAPRLLIYNAKTLADGIPARFSG
SGSGTDYTLTISSLEPEDFASYYCQHFWNTPPTFGAGTKLELKR SEQ ID NO: 19 (polypeptide):
EIVLTQSPGTLSLSPGERATLSCRASGNIHSYLAWYQQKPGQAPRLLIYNAKTLADGIPDRFSG
SGSGTDYTLTISRLEPEDFAVYYCQHFWNTPPTFGAGTKLELKR SEQ ID NO: 20 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSS SEQ ID NO: 21 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY (Fig. 8 continued)
PSDIAVEWESNGQPENNYKTTPPVLDSDGSFFLYSKLTVDKSRWQQGNVFSCSVMHEALHN
HYTQKSLSLSPGK SEQ ID NO: 22 (polypeptide):
QIQLTQSPSFLSASVGDSVTITCRASGNIHSYLAWYQQKPGKAPQLLIYNAKTLADGVPSRFS
GSGSGTEYTLTISSLQPEDFATYYCQHFWNTPPTFGAGTKLELKRTVAAPSVFIFPPSDEQLK
SGTASVVCLLNNFYPREAKVQWKVDNALQSGNSQESVTEQDSKDSTYSLSSTLTLSKADYEK
HKVYACEVTHQGLSSPVTKSFNRGEC SEQ ID NO: 23 (polypeptide):
EIVLTQSPATLSLSPGERATLSCRASGNIHSYLAWYQQKPGQAPRLLIYNAKTLADGIPARFSG
SGSGTDYTLTISSLEPEDFASYYCQHFWNTPPTFGAGTKLELKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC SEQ ID NO: 24 (polypeptide):
EIVLTQSPGTLSLSPGERATLSCRASGNIHSYLAWYQQKPGQAPRLLIYNAKTLADGIPDRFSG
SGSGTDYTLTISRLEPEDFAVYYCQHFWNTPPTFGAGTKLELKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC SEQ ID NO: 25 (DNA):
CAGGTGCAGCTGCAGCAGTCTGGACCTGGCCTAGTGCAGCCCTCACAGAGCCTGTCCAT
AACCTGCACAGTCTCTGGTTTCTCATTAACTAGCTATGGTATACACTGGGTTCGCCAGTCT
CCAGGAAAGGGTCTGGAGTGGCTGGGAGTGATATGGAGAGGTGGAGGCACAGACTCCA
ATGCAGCTTTCATGTCCAGACTGAGCATCACCAAGGACAATTCCAAGAGCCAAGTTTTCTT
TAAAATGAACAGTCTGCAAGCTGATGACACTGCCATATATTACTGTGCCAGAAGTAGGTAC
GACGAGGAGGAAAGTATGAACTACTGGGGTCAAGGAACCTCAGTCACCGTCTCCTCAGC
CAAAACGACACCCCCATCTGTCTATCCACTGGCCCCTGGATCTGCTGCCCAAACTAACTC
CATGGTGACCCTGGGATGCCTGGTCAAGGGCTATTTCCCTGAGCCAGTGACAGTGACCT
GGAACTCTGGATCCCTGTCCAGCGGTGTGCACACCTTCCCAGCTGTCCTGCAGTCTGAC
CTCTACACTCTGAGCAGCTCAGTGACTGTCCCCTCCAGCCCTCGGCCCAGCGAGACCGT
CACCTGCAACGTTGCCCACCCGGCCAGCAGCACCAAGGTGGACAAGAAAATTGTGCCCA
GGGATTGTGGTTGTAAGCCTTGCATATGTACAGTCCCAGAAGTATCATCTGTCTTCATCTT
CCCCCCAAAGCCCAAGGATGTGCTCACCATTACTCTGACTCCTAAGGTCACGTGTGTTGT
GGTAGACATCAGCAAGGATGATCCCGAGGTCCAGTTCAGCTGGTTTGTAGATGATGTGGA
GGTGCACACAGCTCAGACGCAACCCGGGAGGAGCAGTTCAACAGCACTTTCCGCTCAG
TCAGTGAACTTCCCATCATGCACCAGGACTGGCTCAATGGCAAGGAGTTCAAATGCAGGG
TCAACAGTGCAGCTTTCCCTGCCCCATCGAGAAAACCATCTCCAAAACCAAAGGCAGAC
CGAAGGCTCCACAGGTGTACACCATTCCACCTCCCAAGGAGCAGATGGCCAAGGATAAA
GTCAGTCTGACCTGCATGATAACAGACTTCTTCCCTGAAGACATTACTGTGGAGTGGCAG
TGGAATGGGCAGCCAGCGGAGAACTACAAGAACACTCAGCCCATCATGAACACGAATGG
CTCTTACTTCGTCTACAGCAAGCTCAATGTGCAGAAGAGCAACTGGGAGGCAGGAAATAC
TTTCACCTGCTCTGTGTTACATGAGGGCCTGCACAACCACCATACTGAAGAGCCTCTC
CCACTCTCCTGGTAAA SEQ ID NO: 26 (DNA):
CAAATTGTTCTCACCCAGTCTCCAGCCTCCCTATCTGCATCTGTGGGAGAAACTGTCACC
ATCACTTGTCGAGCAAGTGGGAATATTCACAGTTATTTAGCATGGTATCAGCAGAAACAGG
GAAAATCTCCTCAGCTCCTGGTCTATAATGCAAAAACCTTAGCAGATGGTGTGCCATCAAG
GTTCAGTGGCAGTGGATCAGGAACACAATATTCTCTCAAGATCAACAGCCTGCAGCCTGA
AGATTTTGGGAGTTATTACTGTCAACATTTTTGGAATACTCCTCCCACGTTCGGTGCTGGG
ACCAAGCTGGAGCTGAAACGGGCTGATGCTGCACCAACTGTATCCATCTTCCCACCATCC
AGTGAGCAGTTAACATCTGGAGGTGCCTCAGTCGTGTGCTTCTTGAACAACTTCTACCCC (Fig. 8 continued)
AAAGACATCAATGTCAAGTGGAAGATTGATGGCAGTGAACGACAAAATGGCGTCCTGAAC
AGTTGGACTGATCAGGACAGCAAAGACAGCACCTACAGCATGAGCAGCACCCTCACGTT
GACCAAGGACGAGTATGAACGACATAACAGCTATACCTGTGAGGCCACTCACAAGACATC
AACTTCACCCATTGTCAAGAGCTTCAACAGGAATGAGTGT SEQ ID NO: 27 (DNA):
CAGGTGCAGCTGCAGCAGTCTGGACCTGGCCTAGTGCAGCCCTCACAGAGCCTGTCCAT
AACCTGCACAGTCTCTGGTTTCTCATTAACTAGCTATGGTATACACTGGGTTCGCCAGTCT
CCAGGAAAGGGTCTGGAGTGGCTGGGAGTGATATGGAGAGGTGGAGGCACAGACTCCA
ATGCAGCTTTCATGTCCAGACTGAGCATCACCAAGGACAATTCCAAGAGCCAAGTTTTCTT
TAAAATGAACAGTCTGCAAGCTGATGACACTGCCATATATTACTGTGCCAGAAGTAGGTAC
GACGAGGAGGAAAGTATGAACTACTGGGGTCAAGGAACCTCAGTCACCGTCTCCTCA SEQ ID NO: 28 (DNA):
CAAATTGTTCTCACCCAGTCTCCAGCCTCCCTATCTGCATCTGTGGGAGAAACTGTCACC
ATCACTTGTCGAGCAAGTGGGAATATTCACAGTTATTTAGCATGGTATCAGCAGAAACAGG
GAAAATCTCCTCAGCTCCTGGTCTATAATGCAAAAACCTTAGCAGATGGTGTGCCATCAAG
GTTCAGTGGCAGTGGATCAGGAACACAATATTCTCTCAAGATCAACAGCCTGCAGCCTGA
AGATTTTGGGAGTTATTACTGTCAACATTTTTGGAATACTCCTCCCACGTTCGGTGCTGGG
ACCAAGCTGGAGCTGAAA SEQ ID NO: 29 (DNA):
CAGGTGCAGCTGCAGCAGTCTGGACCTGGCCTAGTGCAGCCCTCACAGAGCCTGTCCAT
AACCTGCACAGTCTCTGGTTTCTCATTAACTAGCTATGGTATACACTGGGTTCGCCAGTCT
CCAGGAAAGGGTCTGGAGTGGCTGGGAGTGATATGGAGAGGTGGAGGCACAGACTCCA
ATGCAGCTTTCATGTCCAGACTGAGCATCACCAAGGACAATTCCAAGAGCCAAGTTTTCTT
TAAAATGAACAGTCTGCAAGCTGATGACACTGCCATATATTACTGTGCCAGAAGTAGGTAC
GACGAGGAGGAAAGTATGAACTACTGGGGTCAAGGAACCTCAGTCACCGTCTCCTCAGC
CAGCACCAAGGGCCCCAGCGTGTTCCCCCTGGCCCCCAGCAGCAAGAGCACCAGCGGC
GGCACCGCCGCCCTGGGCTGCCTGGTGAAGGACTACTTCCCCGAGCCCGTGACCGTGA
GCTGGAACAGCGGCGCCCTGACCAGCGGCGTGCACACCTTCCCCGCCGTGCTGCAGAG
CAGCGGCCTGTACAGCCTGAGCAGCGTGGTGACCGTGCCCAGCAGCAGCCTGGGCACC
CAGACCTACATCTGCAACGTGAACCACAAGCCCAGCAACACCAAGGTGGACAAGAAGGT
GGAGCCCAAGAGCTGCGACAAGACCCACACCTGCCCCCCCTGCCCCGCCCCCGAGCTG
CTGGGCGGCCCCAGCGTGTTCCTGTTCCCCCCAAGCCCAAGGACACCCTGATGATCAG
CAGGACCCCCGAGGTGACCTGCGTGGTGGTGGACGTGAGCCACGAGGACCCCGAGGTG
AAGTTCAACTGGTACGTGGACGGCGTGGAGGTGCACAACGCCAAGACCAAGCCCAGGGA
GGAGCAGTACAACAGCACCTACAGGGTGGTGAGCGTGCTGACCGTGCTGCACCAGGACT
GGCTGAACGGCAAGGAGTACAAGTGCAAGGTGAGCAACAAGGCCCTGCCCGCCCCCAT
CGAGAAGACCATCAGCAAGGCCAAGGGCCAGCCCAGGGAGCCCCAGGTGTACACCCTG
CCCCCCAGCAGGGACGAGCTGACCAAGAACCAGGTGAGCCTGACCTGCCTGGTGAAGG
GCTTCTACCCCAGCGACATCGCCGTGGAGTGGGAGAGCAACGGCCAGCCCGAGAACAA
CTACAAGACCACCCCCCCCGTGCTGGACAGCGACGGCAGCTTCTTCCTGTACAGCAAGC
TGACCGTGGACAAGAGCAGGTGGCAGCAGGGCAACGTGTTCAGCTGCAGCGTGATGCA
CGAGGCCCTGCACAACCACTACACCCAGAAGAGCCTGAGCCTGAGCCCCGGCAAG SEQ ID NO: 30 (DNA):
CAAATTGTTCTCACCCAGTCTCCAGCCTCCCTATCTGCATCTGTGGGAGAAACTGTCACC
ATCACTTGTCGAGCAAGTGGGAATATTCACAGTTATTTAGCATGGTATCAGCAGAAACAGG
GAAAATCTCCTCAGCTCCTGGTCTATAATGCAAAAACCTTAGCAGATGGTGTGCCATCAAG
GTTCAGTGGCAGTGGATCAGGAACACAATATTCTCTCAAGATCAACAGCCTGCAGCCTGA
AGATTTTGGGAGTTATTACTGTCAACATTTTTGGAATACTCCTCCCACGTTCGGTGCTGGG
ACCAAGCTGGAGCTGAAACGCACCGTGGCGGCGCCGAGCGTGTTTATTTTTCCGCCGAG
CGATGAACAGCTGAAAAGCGGCACCGCGAGCGTGGTGTGCCTGCTGAACAACTTTTATC (Fig. 8 continued)
CGCGCGAAGCGAAAGTGCAGTGGAAAGTGGATAACGCGCTGCAGAGCGGCAACAGCCA
GGAAAGCGTGACCGAACAGGATAGCAAAGATAGCACCTATAGCCTGAGCAGCACCCTGA
CCCTGAGCAAAGCGGATTATGAAAAACATAAAGTGTATGCGTGCGAAGTGACCCATCAGG
GCCTGAGCAGCCCGGTGACCAAAAGCTTTAACCGCGGCGAATGC SEQ ID NO: 31 (DNA):
GCCAGCACCAAGGGCCCCAGCGTGTTCCCCCTGGCCCCCAGCAGCAAGAGCACCAGCG
GCGGCACCGCCGCCCTGGGCTGCCTGGTGAAGGACTACTTCCCCGAGCCCGTGACCGT
GAGCTGGAACAGCGGCGCCCTGACCAGCGGCGTGCACACCTTCCCCGCCGTGCTGCAG
AGCAGCGGCCTGTACAGCCTGAGCAGCGTGGTGACCGTGCCCAGCAGCAGCCTGGGCA
CCCAGACCTACATCTGCAACGTGAACCACAAGCCCAGCAACACCAAGGTGGACAAGAAG
GTGGAGCCCAAGAGCTGCGACAAGACCCACACCTGCCCCCCCTGCCCCGCCCCCGAGC
TGCTGGGCGGCCCCAGCGTGTTCCTGTTCCCCCCCAAGCCCAAGGACACCCTGATGATC
AGCAGGACCCCCGAGGTGACCTGCGTGGTGGTGGACGTGAGCCACGAGGACCCCGAGG
TGAAGTTCAACTGGTACGTGGACGGCGTGGAGGTGCACAACGCCAAGACCAAGCCCAGG
GAGGAGCAGTACAACAGCACCTACAGGGTGGTGAGCGTGCTGACCGTGCTGCACCAGG
ACTGGCTGAACGGCAAGGAGTACAAGTGCAAGGTGAGCAACAAGGCCCTGCCCGCCCC
CATCGAGAAGACCATCAGCAAGGCCAAGGGCCAGCCCAGGGAGCCCCAGGTGTACACC
CTGCCCCCCAGCAGGGACGAGCTGACCAAGAACCAGGTGAGCCTGACCTGCCTGGTGA
AGGGCTTCTACCCCAGCGACATCGCCGTGGAGTGGGAGAGCAACGGCCAGCCCGAGAA
CAACTACAAGACCACCCCCCCCGTGCTGGACAGCGACGGCAGCTTCTTCCTGTACAGCA
AGCTGACCGTGGACAAGAGCAGGTGGCAGCAGGGCAACGTGTTCAGCTGCAGCGTGAT
GCACGAGGCCCTGCACAACCACTACACCCAGAAGAGCCTGAGCCTGAGCCCCGGCAAG SEQ ID NO: 32 (DNA):
CGCACCGTGGCGGCGCCGAGCGTGTTTATTTTTCCGCCGAGCGATGAACAGCTGAAAAG
CGGCACCGCGAGCGTGGTGTGCCTGCTGAACAACTTTTATCCGCGCGAAGCGAAAGTGC
AGTGGAAAGTGGATAACGCGCTGCAGAGCGGCAACAGCCAGGAAAGCGTGACCGAACA
GGATAGCAAAGATAGCACCTATAGCCTGAGCAGCACCCTGACCCTGAGCAAAGCGGATT
ATGAAAAACATAAAGTGTATGCGTGCGAAGTGACCCATCAGGGCCTGAGCAGCCCGGTG
ACCAAAAGCTTTAACCGCGGCGAATGC SEQ ID NO: 33 (DNA):
<u>CAGGTGCAGCTGCAGGAGAGCGGCCCCGGCCTGGTGAAGCCCAGCGAGACCCTGAGCC
TGACCTGCACCGTGAGCGGCTTCAGCCTGACCAGCTACGGCATCCACTGGATCAGGCAG
AGCCCCGGCAGGGGCCTGGAGTGGATCGGCGTGATCTGGAGGGGCGGCGGCACCGAC
AGCAACGCCGCCTTCATGAGCAGGGTGACCATCAGCAGGGACACCAGCAAGAGCCAGGT
GAGCCTGAAGCTGGGCAGCGTGACCGCCGCCGACACCGCCATCTACTACTGCGCCAGG
AGCAGGTACGACGAGGAGGAGAGCATGAACTACTGGGGCCAGGGCACCAGCGTGACCG
TGAGCAGC</u>

SEQ ID NO: 34 (DNA):
<u>GAAATTGTGCTGACCCAGAGCCCGAGCAGCCTGAGCGCGAGCGTGGGCGATAGCGTGA
CCATTACCTGCCGCGCGAGCGGCAACATTCATAGCTATCTGGCGTGGTATCAGCAGAAAC
CGGGCAAAGCGCCGAAACTGCTGATTTATAACGCGAAAACCCTGGCGGATGGCGTGCCG
AGCCGCTTTAGCGGCAGCGGCAGCGGCACCCAGTATACCCTGACCATTAGCAGCCTGCA
GCCGGAAGATTTTGCGACCTATTATTGCCAGCATTTTTGGAACACCCCGCCGACCTTTGG
CGCGGGCACCAAACTGGAACTGAAA</u>

SEQ ID NO: 35 (DNA):
<u>CAGATTCAGCTGACCCAGAGCCCGAGCTTTCTGAGCGCGAGCGTGGGCGATAGCGTGAC
CATTACCTGCCGCGCGAGCGGCAACATTCATAGCTATCTGGCGTGGTATCAGCAGAAACC
GGGCAAAGCGCCGCAGCTGCTGATTTATAACGCGAAAACCCTGGCGGATGGCGTGCCGA
GCCGCTTTAGCGGCAGCGGCAGCGGCACCGAATATACCCTGACCATTAGCAGCCTGCAG</u>

(Fig. 8 continued)

CCGGAAGATTTTGCGACCTATTATTGCCAGCATTTTTGGAACACCCCGCCGACCTTTGGC
GCGGGCACCAAACTGGAACTGAAA

SEQ ID NO: 36 (DNA):
GAGATCGTGCTGACCCAGAGCCCCGCCACCCTGAGCCTGAGCCCCGGCGAGAGGGCCA
CCCTGAGCTGCAGGGCCAGCGGCAACATCCACAGCTACCTGGCCTGGTACCAGCAGAAG
CCCGGCCAGGCCCCCAGGCTGCTGATCTACAACGCCAAGACCCTGGCCGACGGCATCC
CCGCCAGGTTCAGCGGCAGCGGCAGCGGCACCGACTACACCCTGACCATCAGCAGCCT
GGAGCCCGAGGACTTCGCCAGCTACTACTGCCAGCACTTCTGGAACACCCCCCCCACCT
TCGGCGCCGGCACCAAGCTGGAGCTGAAG

SEQ ID NO: 37 (DNA):
GAGATCGTGCTGACCCAGAGCCCCGGCACCCTGAGCCTGAGCCCCGGCGAGAGGGCCA
CCCTGAGCTGCAGGGCCAGCGGCAACATCCACAGCTACCTGGCCTGGTACCAGCAGAAG
CCCGGCCAGGCCCCCAGGCTGCTGATCTACAACGCCAAGACCCTGGCCGACGGCATCC
CCGACAGGTTCAGCGGCAGCGGCAGCGGCACCGACTACACCCTGACCATCAGCAGGCT
GGAGCCCGAGGACTTCGCCGTGTACTACTGCCAGCACTTCTGGAACACCCCCCCCACCT
TCGGCGCCGGCACCAAGCTGGAGCTGAAG

SEQ ID NO: 38 (DNA):
CAGGTGCAGCTGCAGGAGAGCGGCCCCGGCCTGGTGAAGCCCAGCGAGACCCTGAGCC
TGACCTGCACCGTGAGCGGCTTCAGCCTGACCAGCTACGGCATCCACTGGATCAGGCAG
AGCCCCGGCAGGGGCCTGGAGTGGATCGGCGTGATCTGGAGGGGCGGCGGCACCGAC
AGCAACGCCGCCTTCATGAGCAGGATCACCATCAGCAGGGACACCAGCAAGACCCAGGT
GAGCCTGAAGCTGGGCAGCGTGACCGCCGCCGACACCGCCATCTACTACTGCGCCAGG
AGCAGGTACGACGAGGAGGAGAGCATGAACTACTGGGGCCAGGGCACCAGCGTGACCG
TGAGCAGC

SEQ ID NO: 39 (polypeptide):
QVQLQQSGPGLVQPSQSLSITCTVSGFSLTSYGIHWVRQSPGKGLEWLGVIWRGGGTDSNA
AFMSRLSITKDNSKSQVFFKMNSLQADDTAIYYCARSRYDEEESMNYWGQGTSVTVSSAKTT
PPSVYPLAPGSAAQTNSMVTLGCLVKGYFPEPVTVTWNSGSLSSGVHTFPAVLQSDLYTLSS
SVTVPSSPRPSETVTCNVAHPASSTKVDKKIVPRDCGCKPCICTVPEVSSVFIFPPKPKDVLTIT
LTPKVTCVVVDISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMNTNGSYFVYSKLNVQKSNWEAGNTFTCSVLHEGLHNHHTEKS
LSHSPGKQIVLTQSPASLSASVGETVTITCRASGNIHSYLAWYQQKQGKSPQLLVYNAKTLAD
GVPSRFSGSGSGTQYSLKINSLQPEDFGSYYCQHFWNTPPTFGAGTKLELKRADAAPTVSIF
PPSSEQLTSGGASVVCFLNNFYPKDINVKWKIDGSERQNGVLNSWTDQDSKDSTYSMSSTLT
LTKDEYERHNSYTCEATHKTSTSPIVKSFNRNEC SEQ ID NO: 40 (polypeptide):
QVQLQQSGPGLVQPSQSLSITCTVSGFSLTSYGIHWVRQSPGKGLEWLGVIWRGGGTDSNA
AFMSRLSITKDNSKSQVFFKMNSLQADDTAIYYCARSRYDEEESMNYWGQGTSVTVSSASTK
GPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEAL
HNHYTQKSLSLSPGKQIVLTQSPASLSASVGETVTITCRASGNIHSYLAWYQQKQGKSPQLLV
YNAKTLADGVPSRFSGSGSGTQYSLKINSLQPEDFGSYYCQHFWNTPPTFGAGTKLELKRTV
AAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (Fig. 8 continued)

SEQ ID NO: 41 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPSSLSASVGDSVTITCRASGNIHSYLAWYQQKPGKAPKLLIYNA
KTLADGVPSRFSGSGSGTQYTLTISSLQPEDFATYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 42 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKQIQLTQSPSFLSASVGDSVTITCRASGNIHSYLAWYQQKPGKAPQLLIYNA
KTLADGVPSRFSGSGSGTEYTLTISSLQPEDFATYYCQHFWNTPPTFGAGTKLELKRTVAAPS
VFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC SEQ ID NO: 43 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPATLSLSPGERATLSCRASGNIHSYLAWYQQKPGQAPRLLIYN
AKTLADGIPARFSGSGSGTDYTLTISSLEPEDFASYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 44 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPGTLSLSPGERATLSCRASGNIHSYLAWYQQKPGQAPRLLIYN
AKTLADGIPDRFSGSGSGTDYTLTISRLEPEDFAVYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC (Fig. 8 continued)

SEQ ID NO: 45 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPSSLSASVGDSVTITCRASGNIHSYLAWYQQKPGKAPKLLIYNA
KTLADGVPSRFSGSGSGTQYTLTISSLQPEDFATYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 46 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKQIQLTQSPSFLSASVGDSVTITCRASGNIHSYLAWYQQKPGKAPQLLIYNA
KTLADGVPSRFSGSGSGTEYTLTISSLQPEDFATYYCQHFWNTPPTFGAGTKLELKRTVAAPS
VFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC SEQ ID NO: 47 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPATLSLSPGERATLSCRASGNIHSYLAWYQQKPGQAPRLLIYN
AKTLADGIPARFSGSGSGTDYTLTISSLEPEDFASYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC SEQ ID NO: 48 (polypeptide):
QVQLQESGPGLVKPSETLSLTCTVSGFSLTSYGIHWIRQSPGRGLEWIGVIWRGGGTDSNAA
FMSRITISRDTSKTQVSLKLGSVTAADTAIYYCARSRYDEEESMNYWGQGTSVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHN
HYTQKSLSLSPGKEIVLTQSPGTLSLSPGERATLSCRASGNIHSYLAWYQQKPGQAPRLLIYN
AKTLADGIPDRFSGSGSGTDYTLTISRLEPEDFAVYYCQHFWNTPPTFGAGTKLELKRTVAAP
SVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC (Fig. 8 continued)

SEQ ID NO: 49 (polypeptide):
EVQLVESGGGLVKPGGSLRLSCAASGFTFRSYSMNWVRQAPGKGLEWVSSIISSSSYIYYAD
SVKGRFTISRDNAKNSLYLQMNSLRAEDTALYYCARDQNAMDVWGQGTTVTVSS SEQ ID NO: 50 (polypeptide):
SYELTQPPSVSVAPGKTARITCAGNNIGSKSVHWYQQKPGQAPVLVIYYDSDRPSGIPERFSG
SNSGNTATLTISRVEAGDEADYYCQVWDSGSDHPWVFGGGTKLTVLRQPKAAPSVTLFPPS
SEELQANKATLVCLISDFYPGAVTVAWKADSSPVKAGVETTTPSKQSNNKYAASSYLSLTPEQ
WKSHRSYSCQVTHEGSTVEKTVAPTECS SEQ ID NO: 51 (polypeptide):
EVQLVESGGGLVKPGGSLRLSCAASGFTFSGYSMNWVRQAPGKGLEWVSSISSSSTYIYYV
DSVRGRFTISRDNAKNSLYLQMNSLRAEDTAVYYCARDENDMDVWGQGTTVTVSSGSASAP
TLFPLVSCENSPSDTSSVAVGCLAQDFLPDSITFSWKYKNNSDISSTRGFPSVLRGGKYAATS
QVLLPSKDVMQGTDEHVVCKVQHPNGNKEKNVPLPVIAELPPKVSVFVPPRDGFFGNPRKSK
LICQATGFSPRQIQVSWLREGKQVGSGVTTDQVQAEAKESGPTTYKVTSTLTIKESDWLSQS
MFTCRVDHRGLTFQQNASSMCVPDQDTAIRVFAIPPSFASIFLTKSTKLTCLVTDLTTYDSVTIS
WTRQNGEAVKTHTNISESHPNATFSAVGEASICEDDWNSGERFTCTVTHTDLPSPLKQTISRP
KGVALHRPDVYLLPPAREQLNLRESATITCLVTGFSPADVFVQWMQRGQPLSPEKYVTSAPM
PEPQAPGRYFAHSILTVSEEEWNTGETYTCVVAHEALPNRVTERTVDKSTGKPTLYNVSLVM
SDTAGTCY SEQ ID NO: 52 (polypeptide):
SYVLTQPPSVSVAPGKTARITCGGNNIGTKSVHWYQQKPGQAPVLVIYYDSDRPSGIPERFSG
SNSGNTATLTISRVEAGDEADYYCQVWDSGSDHPWVFGGGTKLTVLRQPKAAPSVTLFPPS
SEELQANKATLVCLISDFYPGAVTVAWKADSSPVKAGVETTTPSKQSNNKYAASSYLSLTPEQ
WKSHRSYSCQVTHEGSTVEKTVAPTECS SEQ ID NO: 53 (polypeptide):
SYELTQPPSVSVAPGKTARITCAGNNIGSKSVHWYQQKPGQAPVLVIYYDSDRPSGIPERFSG
SNSGNTATLTISRVEAGDEADYYCQVWDSGSDHPWVFGGGTKLTVLR

SEQUENCE LISTING

Sequence total quantity: 53
SEQ ID NO: 1          moltype = AA  length = 443
FEATURE               Location/Qualifiers
source                1..443
                      mol_type = protein
                      organism = Mus musculus

```
SEQUENCE: 1
QVQLQQSGPG LVQPSQSLSI TCTVSGFSLT SYGIHWVRQS PGKGLEWLGV IWRGGGTDSN    60
AAFMSRLSIT KDNSKSQVFF KMNSLQADDT AIYYCARSRY DEEESMNYWG QGTSVTVSSA   120
KTTPPSVYPL APGSAAQTNS MVTLGCLVKG YFPEPVTVTW NSGSLSSGVH TFPAVLQSDL   180
YTLSSSVTVP SSPRPSETVT CNVAHPASST KVDKKIVPRD CGCKPCICTV PEVSSVFIFP   240
PKPKDVLTIT LTPKVTCVVV DISKDDPEVQ FSWFVDDVEV HTAQTQPREE QFNSTFRSVS   300
ELPIMHQDWL NGKEFKCRVN SAAFPAPIEK TISKTKGRPK APQVYTIPPP KEQMAKDKVS   360
LTCMITDFFP EDITVEWQWN GQPAENYKNT QPIMNTNGSY FVYSKLNVQK SNWEAGNTFT   420
CSVLHEGLHN HHTEKSLSHS PGK                                          443

SEQ ID NO: 2              moltype = AA  length = 214
FEATURE                   Location/Qualifiers
source                    1..214
                          mol_type = protein
                          organism = Mus musculus
SEQUENCE: 2
QIVLTQSPAS LSASVGETVT ITCRASGNIH SYLAWYQQKQ GKSPQLLVYN AKTLADGVPS    60
RFSGSGSGTQ YSLKINSLQP EDFGSYYCQH FWNTPPTFGA GTKLELKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 3              moltype = AA  length = 119
FEATURE                   Location/Qualifiers
source                    1..119
                          mol_type = protein
                          organism = Mus musculus
SEQUENCE: 3
QVQLQQSGPG LVQPSQSLSI TCTVSGFSLT SYGIHWVRQS PGKGLEWLGV IWRGGGTDSN    60
AAFMSRLSIT KDNSKSQVFF KMNSLQADDT AIYYCARSRY DEEESMNYWG QGTSVTVSS    119

SEQ ID NO: 4              moltype = AA  length = 108
FEATURE                   Location/Qualifiers
source                    1..108
                          mol_type = protein
                          organism = Mus musculus
SEQUENCE: 4
QIVLTQSPAS LSASVGETVT ITCRASGNIH SYLAWYQQKQ GKSPQLLVYN AKTLADGVPS    60
RFSGSGSGTQ YSLKINSLQP EDFGSYYCQH FWNTPPTFGA GTKLELKR                108

SEQ ID NO: 5              moltype = AA  length = 8
FEATURE                   Location/Qualifiers
source                    1..8
                          mol_type = protein
                          organism = Mus musculus
SEQUENCE: 5
GFSLTSYG                                                              8

SEQ ID NO: 6              moltype = AA  length = 7
FEATURE                   Location/Qualifiers
source                    1..7
                          mol_type = protein
                          organism = Mus musculus
SEQUENCE: 6
IWRGGGT                                                               7

SEQ ID NO: 7              moltype = AA  length = 13
FEATURE                   Location/Qualifiers
source                    1..13
                          mol_type = protein
                          organism = Mus musculus
SEQUENCE: 7
ARSRYDEEES MNY                                                       13

SEQ ID NO: 8              moltype = AA  length = 6
FEATURE                   Location/Qualifiers
source                    1..6
                          mol_type = protein
                          organism = Mus musculus
SEQUENCE: 8
GNIHSY                                                                6

SEQ ID NO: 9              moltype = AA  length = 4
FEATURE                   Location/Qualifiers
source                    1..4
                          mol_type = protein
                          organism = Mus musculus
SEQUENCE: 9
NAKT                                                                  4
```

```
SEQ ID NO: 10              moltype = AA   length = 9
FEATURE                    Location/Qualifiers
source                     1..9
                           mol_type = protein
                           organism = Mus musculus
SEQUENCE: 10
QHFWNTPPT                                                                9

SEQ ID NO: 11              moltype = AA   length = 449
FEATURE                    Location/Qualifiers
source                     1..449
                           mol_type = protein
                           organism = synthetic construct
SEQUENCE: 11
QVQLQQSGPG LVQPSQSLSI TCTVSGFSLT SYGIHWVRQS PGKGLEWLGV IWRGGGTDSN    60
AAFMSRLSIT KDNSKSQVFF KMNSLQADDT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 12              moltype = AA   length = 214
FEATURE                    Location/Qualifiers
source                     1..214
                           mol_type = protein
                           organism = synthetic construct
SEQUENCE: 12
QIVLTQSPAS LSASVGETVT ITCRASGNIH SYLAWYQQKQ GKSPQLLVYN AKTLADGVPS    60
RFSGSGSGTQ YSLKINSLQP EDFGSYYCQH FWNTPPTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 13              moltype = AA   length = 449
FEATURE                    Location/Qualifiers
source                     1..449
                           mol_type = protein
                           organism = synthetic construct
SEQUENCE: 13
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 14              moltype = AA   length = 214
FEATURE                    Location/Qualifiers
source                     1..214
                           mol_type = protein
                           organism = synthetic construct
SEQUENCE: 14
EIVLTQSPSS LSASVGDSVT ITCRASGNIH SYLAWYQQKP GKAPKLLIYN AKTLADGVPS    60
RFSGSGSGTQ YTLTISSLQP EDFATYYCQH FWNTPPTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 15              moltype = AA   length = 119
FEATURE                    Location/Qualifiers
source                     1..119
                           mol_type = protein
                           organism = synthetic construct
SEQUENCE: 15
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSS    119

SEQ ID NO: 16              moltype = AA   length = 108
FEATURE                    Location/Qualifiers
source                     1..108
                           mol_type = protein
                           organism = synthetic construct
SEQUENCE: 16
EIVLTQSPSS LSASVGDSVT ITCRASGNIH SYLAWYQQKP GKAPKLLIYN AKTLADGVPS    60
RFSGSGSGTQ YTLTISSLQP EDFATYYCQH FWNTPPTFGA GTKLELKR                108

SEQ ID NO: 17              moltype = AA   length = 108
```

```
FEATURE                     Location/Qualifiers
source                      1..108
                            mol_type = protein
                            organism = synthetic construct
SEQUENCE: 17
QIQLTQSPSF LSASVGDSVT ITCRASGNIH SYLAWYQQKP GKAPQLLIYN AKTLADGVPS    60
RFSGSGSGTE YTLTISSLQP EDFATYYCQH FWNTPPTFGA GTKLELKR                108

SEQ ID NO: 18               moltype = AA   length = 108
FEATURE                     Location/Qualifiers
source                      1..108
                            mol_type = protein
                            organism = synthetic construct
SEQUENCE: 18
EIVLTQSPAT LSLSPGERAT LSCRASGNIH SYLAWYQQKP GQAPRLLIYN AKTLADGIPA    60
RFSGSGSGTD YTLTISSLEP EDFASYYCQH FWNTPPTFGA GTKLELKR                108

SEQ ID NO: 19               moltype = AA   length = 108
FEATURE                     Location/Qualifiers
source                      1..108
                            mol_type = protein
                            organism = synthetic construct
SEQUENCE: 19
EIVLTQSPGT LSLSPGERAT LSCRASGNIH SYLAWYQQKP GQAPRLLIYN AKTLADGIPD    60
RFSGSGSGTD YTLTISRLEP EDFAVYYCQH FWNTPPTFGA GTKLELKR                108

SEQ ID NO: 20               moltype = AA   length = 119
FEATURE                     Location/Qualifiers
source                      1..119
                            mol_type = protein
                            organism = synthetic construct
SEQUENCE: 20
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSS    119

SEQ ID NO: 21               moltype = AA   length = 449
FEATURE                     Location/Qualifiers
source                      1..449
                            mol_type = protein
                            organism = synthetic construct
SEQUENCE: 21
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 22               moltype = AA   length = 214
FEATURE                     Location/Qualifiers
source                      1..214
                            mol_type = protein
                            organism = synthetic construct
SEQUENCE: 22
QIQLTQSPSF LSASVGDSVT ITCRASGNIH SYLAWYQQKP GKAPQLLIYN AKTLADGVPS    60
RFSGSGSGTE YTLTISSLQP EDFATYYCQH FWNTPPTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 23               moltype = AA   length = 214
FEATURE                     Location/Qualifiers
source                      1..214
                            mol_type = protein
                            organism = synthetic construct
SEQUENCE: 23
EIVLTQSPAT LSLSPGERAT LSCRASGNIH SYLAWYQQKP GQAPRLLIYN AKTLADGIPA    60
RFSGSGSGTD YTLTISSLEP EDFASYYCQH FWNTPPTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 24               moltype = AA   length = 214
FEATURE                     Location/Qualifiers
source                      1..214
                            mol_type = protein
                            organism = synthetic construct
SEQUENCE: 24
EIVLTQSPGT LSLSPGERAT LSCRASGNIH SYLAWYQQKP GQAPRLLIYN AKTLADGIPD    60
```

```
RFSGSGSGTD YTLTISRLEP EDFAVYYCQH FWNTPPTFGA GTKLELKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 25           moltype = DNA   length = 1329
FEATURE                 Location/Qualifiers
source                  1..1329
                        mol_type = other DNA
                        organism = synthetic construct
SEQUENCE: 25
caggtgcagc tgcagcagtc tggacctggc ctagtgcagc cctcacagag cctgtccata      60
acctgcacag tctctggttt ctcattaact agctatggta tacactgggt tcgccagtct     120
ccaggaaagg gtctggagtg gctgggagtg atatggagag gtggaggcac agactccaat     180
gcagctttca tgtccagact gagcatcacc aaggacaatt ccaagagcca gttttcctt      240
aaaatgaaca gtctgcaagc tgatgacact gccatatatt actgtgccag aagtaggtac     300
gacgaggagg aaagtatgaa ctactggggt caaggaacct cagtcaccgt ctcctcagcc     360
aaaacgacac ccccatctgt ctatccactg gcccctggat ctgctgccca aactaactcc     420
atggtgaccc tgggatgcct ggtcaagggc tatttccctg agccagtgac agtgacctgg     480
aactctggat ccctgtccag cggtgtgcac accttcccag ctgtcctgca gtctgacctc     540
tacactctga gcagctcagt gactgtcccc tccagccctc ggcccagcga gaccgtcacc     600
tgcaacgttg cccaccccgg cagcagcacc aaggtggaca gaaaattgtg cccaggggat     660
tgtggttgta agccttgcat atgtacagtc cagaagtatc catctgtctt catcttccc      720
ccaaagccca aggatgtgct caccattact ctgactccta aggtcacgtg tgttgtggta     780
gacatcagca aggatgatcc cgaggtccag ttcagctggt ttgtagatga tgtggaggtg     840
cacacagctc agacgcaacc ccgggaggag cagttcaaca gcactttccg ctcagtcagt     900
gaacttccca tcatgcacca ggactggctc aatggcaagg agttcaaatg cagggtcaac     960
agtgcagctt tccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaga cttcttccct gaagacatta ctgtggagtg gcagtggaat    1140
gggcagccag cggagaacta caagaacact cagcccatca tgaacacgac tggctcttac    1200
ttcgtctaca gcaagctcaa tgtgcagaag agcaactggg aggcaggaaa tactttcacc    1260
tgctctgtgt tacatgaggg cctgcacaac accatactg agaagagcct ctcccactct    1320
cctggtaaa                                                           1329

SEQ ID NO: 26           moltype = DNA   length = 642
FEATURE                 Location/Qualifiers
source                  1..642
                        mol_type = other DNA
                        organism = synthetic construct
SEQUENCE: 26
caaattgttc tcacccagtc tccagcctcc ctatctgcat ctgtgggaga aactgtcacc      60
atcacttgtc gagcaagtgg gaatattcac agttatttag catggtatca gcagaaacag     120
ggaaaatctc ctcagctcct ggtctataat gcaaaaacct tagcagatgg tgtgccatca     180
aggttcagtg gcagtggatc aggaacacaa tattctctca gatcaacag cctgcagcct     240
gaagatttg ggagttatta ctgtcaacat ttttggaata ctcctcccac gttcggtgct     300
gggaccaagc tggagctgaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctacg     540
ttgaccaagg acgagtatga acgacataac agctatacct gtgaggccac tcacaagaca     600
tcaacttcac ccattgtcaa gagcttcaac aggaatgagt gt                       642

SEQ ID NO: 27           moltype = DNA   length = 357
FEATURE                 Location/Qualifiers
source                  1..357
                        mol_type = other DNA
                        organism = synthetic construct
SEQUENCE: 27
caggtgcagc tgcagcagtc tggacctggc ctagtgcagc cctcacagag cctgtccata      60
acctgcacag tctctggttt ctcattaact agctatggta tacactgggt tcgccagtct     120
ccaggaaagg gtctggagtg gctgggagtg atatggagag gtggaggcac agactccaat     180
gcagctttca tgtccagact gagcatcacc aaggacaatt ccaagagcca gttttcttt     240
aaaatgaaca gtctgcaagc tgatgacact gccatatatt actgtgccag aagtaggtac     300
gacgaggagg aaagtatgaa ctactggggt caaggaacct cagtcaccgt ctcctca       357

SEQ ID NO: 28           moltype = DNA   length = 321
FEATURE                 Location/Qualifiers
source                  1..321
                        mol_type = other DNA
                        organism = synthetic construct
SEQUENCE: 28
caaattgttc tcacccagtc tccagcctcc ctatctgcat ctgtgggaga aactgtcacc      60
atcacttgtc gagcaagtgg gaatattcac agttatttag catggtatca gcagaaacag     120
ggaaaatctc ctcagctcct ggtctataat gcaaaaacct tagcagatgg tgtgccatca     180
aggttcagtg gcagtggatc aggaacacaa tattctctca gatcaacag cctgcagcct     240
gaagatttg ggagttatta ctgtcaacat ttttggaata ctcctcccac gttcggtgct     300
gggaccaagc tggagctgaa a                                              321

SEQ ID NO: 29           moltype = DNA   length = 1347
```

```
FEATURE                 Location/Qualifiers
source                  1..1347
                        mol_type = other DNA
                        organism = synthetic construct
SEQUENCE: 29
caggtgcagc tgcagcagtc tggacctggc ctagtgcagc cctcacagag cctgtccata    60
acctgcacag tctctggttt ctcattaact agctatggta tacactgggt tcgccagtct   120
ccaggaaagg gtctggagtg gctgggagtg atatggagag gtggaggcac agactccaat   180
gcagctttca tgtccagact gagcatcacc aaggacaatt ccaagagcca agtttttctt   240
aaaatgaaca gtctgcaagc tgatgacact gccatatatt actgtgccag aagtaggtac   300
gacgaggagg aaagtatgaa ctactgggt caaggaacct cagtcaccgt ctcctcagcc   360
agcaccaagg gcccagcgt gttccccctg gccccagca gcaagagcac cagcggcggc   420
accgccgccc tgggctgcct ggtgaaggac tacttcccg agcccgtgac cgtgagctgg   480
aacagcggcg ccctgaccag cggcgtgcac accttcccg ccgtgctga gcagcagcgg   540
ctgtacagcc tgagcagcgt ggtgaccgtg cccagcagca gcctgggcac ccagacctac   600
atctgcaacg tgaaccacaa gcccagcaac accaaggtgg acaagaaggt ggagcccaag   660
agctgcgaca gacccacac ctgccccccc tgccccgccc cgagctgct gggcggcccc   720
agcgtgttcc tgttccccc caagcccaag gacaccctga tgatcagcag gacccccgag   780
gtgacctgcg tggtggtgga cgtgagccac gaggacccg aggtgaagtt caactgtac   840
gtggacggcg tggaggtgca aacgccaag accaagccca gggaggagca gtacaacagc   900
acctacaggg tggtgagcgt gctgaccgtg ctgcaccagg actggctgaa cggcaaggag   960
tacaagtgca aggtgagcaa caaggccctg cccgcccc tcgagaagac catcagcaag  1020
gccaagggcc agcccaggga gcccaggtg tacaccctgc ccccagcag ggacgagctg  1080
accaagaacc aggtgagcct gacctgcctg gtgaagggct ctacccag cgacatcgcc  1140
gtggagtggg agagcaacgg ccagcccgag aacaactaca gaccacccc cccgtgctg  1200
gacagcgacg gcagcttctt cctgtacagc aagctgaccg tggacaagag caggtggcag  1260
cagggcaacg tgttcagctg cagcgtgatg cacgaggccc tgcacaacca ctacacccag  1320
aagagcctga gcctgagccc cggcaag                                      1347

SEQ ID NO: 30           moltype = DNA length = 642
FEATURE                 Location/Qualifiers
source                  1..642
                        mol_type = other DNA
                        organism = synthetic construct
SEQUENCE: 30
caaattgttc tcacccagtc tccagcctcc ctatctgcat ctgtgggaga aactgtcacc    60
atcacttgtc gagcaagtgg gaatattcac agttatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca agatcaacag cctgcagcct   240
gaagattttg ggagttatta ctgtcaacat ttttggaata ctcctccac gttcggtgct   300
gggaccaagc tggagctgaa acgcaccgtg gcggcgccga gcgtgtttat ttttccgccg   360
agcgatgaac agctgaaaag cggcaccgcg agcgtggtgt gcctgctgaa caactttat   420
ccgcgcgaag cgaaagtgca gtggaaagtg gataacgcc tgcagagcgg caacagccag   480
gaaagcgtga ccgaacagga tagcaaagat agcacctata gcctgagcag cacccctgacc   540
ctgagcaaag cggattatga aaaacataaa gtgtatgcgt gcgaagtgac ccatcagggc   600
ctgagcagcc cggtgaccaa aagctttaac cgcggcgaat gc                     642

SEQ ID NO: 31           moltype = DNA length = 990
FEATURE                 Location/Qualifiers
source                  1..990
                        mol_type = other DNA
                        organism = synthetic construct
SEQUENCE: 31
gccagcacca agggccccag cgtgttcccc ctggccccca gcagcaagag caccagcggc    60
ggcaccgccg ccctgggctg cctggtgaag gactactttc ccgagcccgt gaccgtgagc   120
tggaacagcg gcgccctgac cagcggcgtg cacaccttcc ccgccgtgct gcagagcagc   180
ggcctgtaca gcctgagcag cgtggtgacc gtgcccagca gcagcctggg cacccagacc   240
tacatctgca acgtgaacca caagcccagc aacaccaagg tggacaagaa ggtggagccc   300
aagagctgcg acaagaccca cacctgcccc ccctgccccg cccccgagct gctgggcggc   360
ccagcgtgt tcctgttccc ccccaagccc aaggacaccc tgatgatcag caggacccc   420
gaggtgacct gcgtggtggt ggacgtgagc cacgaggacc ccgaggtgaa gttcaactgg   480
tacgtggacg gcgtggaggt gcacaacgcc aagaccaagc caggaggag cagtacaac   540
agcacctaca gggtggtgag cgtgctgacc gtgctgcacc aggactggct gaacggcaag   600
gagtacaagt gcaaggtgag caacaaggcc ctgccccgccc ccatcgagaa gaccatcagc   660
aaggccaagg gccagcccag ggagcccag gtgtacaccc tgcccccag cagggacgag   720
ctgaccaaga accaggtgag cctgacctgc ctggtgaagg gcttctaccc cagcgacatc   780
gccgtggagt gggagagcaa cggccagccc gagaacaact acaagaccac ccccccgtg   840
ctggacagcg acggcagctt cttcctgtac agcaagctga ccgtggacaa gagcaggtgg   900
cagcagggca acgtgttcag ctgcagcgtg atgcacgagg ccctgcacaa ccactacacc   960
cagaagagcc tgagcctgag cccccggcaag                                   990

SEQ ID NO: 32           moltype = DNA length = 321
FEATURE                 Location/Qualifiers
source                  1..321
                        mol_type = other DNA
                        organism = synthetic construct
SEQUENCE: 32
cgcaccgtgg cggcgccgag cgtgtttatt tttccgccga gcgatgaaca gctgaaaagc    60
ggcaccgcga gcgtggtgtg cctgctgaac aactttatc cgcgcgaagc gaaagtgcag   120
```

```
tggaaagtgg ataacgcgct gcagagcggc aacagccagg aaagcgtgac cgaacaggat   180
agcaaagata gcacctatag cctgagcagc accctgaccc tgagcaaagc ggattatgaa   240
aaacataaag tgtatgcgtg cgaagtgacc catcagggcc tgagcagccc ggtgaccaaa   300
agctttaacc gcggcgaatg c                                             321

SEQ ID NO: 33         moltype = DNA  length = 357
FEATURE               Location/Qualifiers
source                1..357
                      mol_type = other DNA
                      organism = synthetic construct
SEQUENCE: 33
caggtgcagc tgcaggagag cggccccggc ctggtgaagc ccagcgagac cctgagcctg   60
acctgcaccg tgagcggctt cagcctgacc agctacggca tccactggat caggcagagc   120
cccggcaggg gcctggagtg gatcggcgtg atctggaggg gcggcggcac cgacagcagc   180
gccgccttca tgagcagggt gaccatcagc agggacacca gcaagagcca ggtgagcctg   240
aagctgggca gcgtgaccgc cgccgacacc gccatctact actgcgccag gagcaggtac   300
gacgaggagg agagcatgaa ctactggggc cagggcacca cgtgaccgt gagcagc       357

SEQ ID NO: 34         moltype = DNA  length = 321
FEATURE               Location/Qualifiers
source                1..321
                      mol_type = other DNA
                      organism = synthetic construct
SEQUENCE: 34
gaaattgtgc tgacccagag cccgagcagc ctgagcgcga gcgtgggcga tagcgtgacc   60
attacctgcc gcgcgagcgg caacattcat agctatctgg cgtggtatca gcagaaaccg   120
ggcaaagcgc cgaaactgct gatttataac gcgaaaaccc tggcggatgg cgtgccgagc   180
cgctttagcg gcagcggcag cggcacccag tataccctga ccattagcag cctgcagccg   240
gaagattttg cgacctatta ttgccagcat ttttggaaca ccccgccgac ctttggcgcg   300
ggcaccaaac tggaactgaa a                                             321

SEQ ID NO: 35         moltype = DNA  length = 321
FEATURE               Location/Qualifiers
source                1..321
                      mol_type = other DNA
                      organism = synthetic construct
SEQUENCE: 35
cagattcagc tgacccagag cccgagcttt ctgagcgcga gcgtgggcga tagcgtgacc   60
attacctgcc gcgcgagcgg caacattcat agctatctgg cgtggtatca gcagaaaccg   120
ggcaaagcgc cgcagctgct gatttataac gcgaaaaccc tggcggatgg cgtgccgagc   180
cgctttagcg gcagcggcag cggcaccgaa tataccctga ccattagcag cctgcagccg   240
gaagattttg cgacctatta ttgccagcat ttttggaaca ccccgccgac ctttggcgcg   300
ggcaccaaac tggaactgaa a                                             321

SEQ ID NO: 36         moltype = DNA  length = 321
FEATURE               Location/Qualifiers
source                1..321
                      mol_type = other DNA
                      organism = synthetic construct
SEQUENCE: 36
gagatcgtgc tgacccagag ccccgccacc ctgagcctga gcccggcga gagggccacc   60
ctgagctgca gggccagcgg caacatccac agctacctgg cctggtacca gcagaagccc   120
ggccaggccc ccaggctgct gatctacaac gccaagaccc tggccgacgg catccccgcc   180
aggttcagcg gcagcggcag cggcaccgac tacaccctga ccatcagcag cctggagccc   240
gaggacttcg ccagctacta ctgccagcac ttctggaaca ccccccccac cttcggcgcc   300
ggcaccaagc tggagctgaa g                                             321

SEQ ID NO: 37         moltype = DNA  length = 321
FEATURE               Location/Qualifiers
source                1..321
                      mol_type = other DNA
                      organism = synthetic construct
SEQUENCE: 37
gagatcgtgc tgacccagag ccccggcacc ctgagcctga gccccggcga gagggccacc   60
ctgagctgca gggccagcgg caacatccac agctacctgg cctggtacca gcagaagccc   120
ggccaggccc ccaggctgct gatctacaac gccaagaccc tggccgacgg catccccgac   180
aggttcagcg gcagcggcag cggcaccgac tacaccctga ccatcagcag gctggagccc   240
gaggacttcg ccgtgtacta ctgccagcac ttctggaaca ccccccccac cttcggcgcc   300
ggcaccaagc tggagctgaa g                                             321

SEQ ID NO: 38         moltype = DNA  length = 357
FEATURE               Location/Qualifiers
source                1..357
                      mol_type = other DNA
                      organism = synthetic construct
SEQUENCE: 38
caggtgcagc tgcaggagag cggccccggc ctggtgaagc ccagcgagac cctgagcctg   60
acctgcaccg tgagcggctt cagcctgacc agctacggca tccactggat caggcagagc   120
cccggcaggg gcctggagtg gatcggcgtg atctggaggg cggcggcac cgacagcaac   180
```

```
gccgccttca tgagcaggat caccatcagc agggacacca gcaagaccca ggtgagcctg    240
aagctgggca gcgtgaccgc cgccgacacc gccatctact actgcgccag gagcaggtac    300
gacgaggagg agagcatgaa ctactggggc cagggcacca gcgtgaccgt gagcagc       357
```

```
SEQ ID NO: 39            moltype = AA   length = 657
FEATURE                  Location/Qualifiers
source                   1..657
                         mol_type = protein
                         organism = synthetic construct
SEQUENCE: 39
QVQLQQSGPG LVQPSQSLSI TCTVSGFSLT SYGIHWVRQS PGKGLEWLGV IWRGGGTDSN     60
AAFMSRLSIT KDNSKSQVFF KMNSLQADDT AIYYCARSRY DEEESMNYWG QGTSVTVSSA    120
KTTPPSVYPL APGSAAQTNS MVTLGCLVKG YFPEPVTVTW NSGSLSSGVH TFPAVLQSDL    180
YTLSSSVTVP SSPRPSETVT CNVAHPASST KVDKKIVPRD CGCKPCICTV PEVSSVFIFP    240
PKPKDVLTIT LTPKVTCVVV DISKDDPEVQ FSWFVDDVEV HTAQTQPREE QFNSTFRSVS    300
ELPIMHQDWL NGKEFKCRVN SAAFPAPIEK TISKTKGRPK APQVYTIPPP KEQMAKDKVS    360
LTCMITDFFP EDITVEWQWN GQPAENYKNT QPIMNTNGSY FVYSKLNVQK SNWEAGNTFT    420
CSVLHEGLHN HHTEKSLSHS PGKQIVLTQS PASLSASVGE TVTITCRASG NIHSYLAWYQ    480
QKQGKSPQLL VYNAKTLADG VPSRFSGSGS GTQYSLKINS LQPEDFGSYY CQHFWNTPPT    540
FGAGTKLELK RADAAPTVSI FPPSSEQLTS GGASVVCFLN NFYPKDINVK WKIDGSERQN    600
GVLNSWTDQD SKDSTYSMSS TLTLTKDEYE RHNSYTCEAT HKTSTSPIVK SFNRNEC       657
```

```
SEQ ID NO: 40            moltype = AA   length = 663
FEATURE                  Location/Qualifiers
source                   1..663
                         mol_type = protein
                         organism = synthetic construct
SEQUENCE: 40
QVQLQQSGPG LVQPSQSLSI TCTVSGFSLT SYGIHWVRQS PGKGLEWLGV IWRGGGTDSN     60
AAFMSRLSIT KDNSKSQVFF KMNSLQADDT AIYYCARSRY DEEESMNYWG QGTSVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGKQ IVLTQSPASL SASVGETVTI TCRASGNIHS    480
YLAWYQQKQG KSPQLLVYNA KTLADGVPSR FSGSGSGTQY SLKINSLQPE DFGSYYCQHF    540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR    660
GEC                                                                  663
```

```
SEQ ID NO: 41            moltype = AA   length = 663
FEATURE                  Location/Qualifiers
source                   1..663
                         mol_type = protein
                         organism = synthetic construct
SEQUENCE: 41
QVQLQESGPG LVKPSETLSL TCTVSGFSLT SYGIHWIRQS PGRGLEWIGV IWRGGGTDSN     60
AAFMSRITIS RDTSKTQVSL KLGSVTAADT AIYYCARSRY DEEESMNYWG QGTSVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGKE IVLTQSPASL SASVGDSVTI TCRASGNIHS    480
YLAWYQQKPG KAPKLLIYNA KTLADGVPSR FSGSGSGTQY TLTISSLQPE DFATYYCQHF    540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR    660
GEC                                                                  663
```

```
SEQ ID NO: 42            moltype = AA   length = 663
FEATURE                  Location/Qualifiers
source                   1..663
                         mol_type = protein
                         organism = synthetic construct
SEQUENCE: 42
QVQLQESGPG LVKPSETLSL TCTVSGFSLT SYGIHWIRQS PGRGLEWIGV IWRGGGTDSN     60
AAFMSRITIS RDTSKTQVSL KLGSVTAADT AIYYCARSRY DEEESMNYWG QGTSVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGKQ IQLTQSPSFL SASVGDSVTI TCRASGNIHS    480
YLAWYQQKPG KAPQLLIYNA KTLADGVPSR FSGSGSGTEY TLTISSLQPE DFATYYCQHF    540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR    660
GEC                                                                  663
```

| SEQ ID NO: 43 | moltype = AA length = 663 |
| --- | --- |
| FEATURE | Location/Qualifiers |
| source | 1..663 |
| | mol_type = protein |
| | organism = synthetic construct |

SEQUENCE: 43

```
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKE IVLTQSPATL SLSPGERATL SCRASGNIHS   480
YLAWYQQKPG QAPRLLIYNA KTLADGIPAR FSGSGSGTDY TLTISSLEPE DFASYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                663
```

| SEQ ID NO: 44 | moltype = AA length = 663 |
| --- | --- |
| FEATURE | Location/Qualifiers |
| source | 1..663 |
| | mol_type = protein |
| | organism = synthetic construct |

SEQUENCE: 44

```
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKE IVLTQSPGTL SLSPGERATL SCRASGNIHS   480
YLAWYQQKPG QAPRLLIYNA KTLADGIPDR FSGSGSGTDY TLTISRLEPE DFAVYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                663
```

| SEQ ID NO: 45 | moltype = AA length = 663 |
| --- | --- |
| FEATURE | Location/Qualifiers |
| source | 1..663 |
| | mol_type = protein |
| | organism = synthetic construct |

SEQUENCE: 45

```
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKE IVLTQSPSSL SASVGDSVTI TCRASGNIHS   480
YLAWYQQKPG KAPKLLIYNA KTLADGVPSR FSGSGSGTQY TLTISSLQPE DFATYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                663
```

| SEQ ID NO: 46 | moltype = AA length = 663 |
| --- | --- |
| FEATURE | Location/Qualifiers |
| source | 1..663 |
| | mol_type = protein |
| | organism = synthetic construct |

SEQUENCE: 46

```
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKQ IQLTQSPSFL SASVGDSVTI TCRASGNIHS   480
YLAWYQQKPG KAPQLLIYNA KTLADGVPSR FSGSGSGTEY TLTISSLQPE DFATYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                663
```

| SEQ ID NO: 47 | moltype = AA length = 663 |
| --- | --- |
| FEATURE | Location/Qualifiers |
| source | 1..663 |

```
                        mol_type = protein
                        organism = synthetic construct
SEQUENCE: 47
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKE IVLTQSPATL SLSPGERATL SCRASGNIHS   480
YLAWYQQKPG QAPRLLIYNA KTLADGIPAR FSGSGSGTDY TLTISSLEPE DFASYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                 663

SEQ ID NO: 48           moltype = AA  length = 663
FEATURE                 Location/Qualifiers
source                  1..663
                        mol_type = protein
                        organism = synthetic construct
SEQUENCE: 48
QVQLQESGPG LVKPSETLSL TCTVSGFSLT SYGIHWIRQS PGRGLEWIGV IWRGGGTDSN    60
AAFMSRITIS RDTSKTQVSL KLGSVTAADT AIYYCARSRY DEEESMNYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKE IVLTQSPGTL SLSPGERATL SCRASGNIHS   480
YLAWYQQKPG QAPRLLIYNA KTLADGIPDR FSGSGSGTDY TLTISRLEPE DFAVYYCQHF   540
WNTPPTFGAG TKLELKRTVA APSVIFPPS DEQLKSGTAS VVCLLNNFYP REAKVQWKVD    600
NALQSGNSQE SVTEQDSKDS TYSLSSTLTL SKADYEKHKV YACEVTHQGL SSPVTKSFNR   660
GEC                                                                 663

SEQ ID NO: 49           moltype = AA  length = 116
FEATURE                 Location/Qualifiers
source                  1..116
                        mol_type = protein
                        organism = Homo sapiens
SEQUENCE: 49
EVQLVESGGG LVKPGGSLRL SCAASGFTFR SYSMNWVRQA PGKGLEWVSS IISSSSYIYY    60
ADSVKGRFTI SRDNAKNSLY LQMNSLRAED TALYYCARDQ NAMDVWGQGT TVTVSS       116

SEQ ID NO: 50           moltype = AA  length = 215
FEATURE                 Location/Qualifiers
source                  1..215
                        mol_type = protein
                        organism = Homo sapiens
SEQUENCE: 50
SYELTQPPSV SVAPGKTARI TCAGNNIGSK SVHWYQQKPG QAPVLVIYYD SDRPSGIPER    60
FSGSNSGNTA TLTISRVEAG DEADYYCQVW DSGSDHPWVF GGGTKLTVLR QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                              215

SEQ ID NO: 51           moltype = AA  length = 569
FEATURE                 Location/Qualifiers
source                  1..569
                        mol_type = protein
                        organism = Homo sapiens
SEQUENCE: 51
EVQLVESGGG LVKPGGSLRL SCAASGFTFS GYSMNWVRQA PGKGLEWVSS ISSSSTYIYY    60
VDSVRGRFTI SRDNAKNSLY LQMNSLRAED TAVYYCARDE NDMDVWGQGT TVTVSSGSAS   120
APTLFPLVSC ENSPSDTSSV AVGCLAQDFL PDSITFSWKY KNNSDISSTR GFPSVLRGGK   180
YAATSQVLLP SKDVMQGTDE HVVCKVQHPN GNKEKNVPLP VIAELPPKVS VFVPPRDGFF   240
GNPRKSKLIC QATGFSPRQI QVSWLREGKQ VGSGVTTDQV QAEAKESGPT TYKVTSTLTI   300
KESDWLSQSM FTCRVDHRGL TFQQNASSMC VPDQDTAIRV FAIPPSFASI FLTKSTKLTC   360
LVTDLTTYDS VTISWTRQNG EAVKTHTNIS ESHPNATFSA VGEASICEDD WNSGERFTCT   420
VTHTDLPSPL KQTISRPKGV ALHRPDVYLL PPAREQLNLR ESATITCLVT GFSPADVFVQ   480
WMQRGQPLSP EKYVTSAPMP EPQAPGRYFA HSILTVSEEE WNTGETYTCV VAHEALPNRV   540
TERTVDKSTG KPTLYNVSLV MSDTAGTCY                                     569

SEQ ID NO: 52           moltype = AA  length = 215
FEATURE                 Location/Qualifiers
source                  1..215
                        mol_type = protein
                        organism = Homo sapiens
SEQUENCE: 52
SYVLTQPPSV SVAPGKTARI TCGGNNIGTK SVHWYQQKPG QAPVLVIYYD SDRPSGIPER    60
```

```
FSGSNSGNTA TLTISRVEAG DEADYYCQVW DSGSDHPWVF GGGTKLTVLR QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                               215

SEQ ID NO: 53           moltype = AA   length = 110
FEATURE                 Location/Qualifiers
source                  1..110
                        mol_type = protein
                        organism = Homo sapiens
SEQUENCE: 53
SYELTQPPSV SVAPGKTARI TCAGNNIGSK SVHWYQQKPG QAPVLVIYYD SDRPSGIPER     60
FSGSNSGNTA TLTISRVEAG DEADYYCQVW DSGSDHPWVF GGGTKLTVLR                110
```

ANTIBODIES TARGETING THE B-CELL RECEPTOR OF CHRONIC LYMPHOCYTIC LEUKEMIA AND USES THEREOF

This application claims priority to EP22156205, filed Feb. 10, 2022, which is incorporated herein by reference in its entirety.

The instant application contains a Sequence Listing which has been submitted electronically in XML file format and is hereby incorporated by reference in its entirety. Said XML copy, image quality created on Jan. 27, 2023, is named 32501_301701_SL.xml and is 66,075 bytes in size.

The present invention provides antibodies for the treatment of chronic lymphocytic leukemia (CLL). These antibodies target the B-cell receptor (BCR) of CLL cells characterised by R110-mutated immunoglobulin lambda variable 3-21 (IGLV3-21$^{R110}$).

The invention also provides nucleic acid sequences encoding the forgoing antibodies, vectors containing the same, pharmaceutical compositions and kits with instructions for use.

BACKGROUND OF THE INVENTION

Antibody therapeutics have been proven to be very effective reagents for the treatment of Leukemias and Lymphomas originating from malignant transformations of B-lineage cells. Since the approval of monoclonal antibodies such as Rituximab, response rates, long-term outcomes, and life-quality of patients with CLL have remarkably improved.

CLL is a heterogeneous, B-lymphocyte-derived malignancy resulting from the clonal proliferation of a CD5-positive subpopulation of B lymphocytes which progressively accumulate in the bone marrow, lymph nodes, peripheral blood and spleen (Roz-man C, Montserrat E. Chronic lymphocytic leukemia. N Engl J Med. 1995; 333: 1052-1057). The disease is the most common type of leukemia in western countries and typically occurs in elderly patients, with a two-fold increased risk of developing CLL for men compared to women (Kipps T J, Stevenson F K, Wu C J, Croce C M, Packham G, Wierda W G, et al. Chronic lymphocytic leukemia. Nat Rev Dis Primers (2017) 3:1-12).

Clinical and biological evidence has shown that the BCR is one of the major factors in clonal selection and survival of CLL cells as reviewed by Burger and Chiorazzi (Burger J A, Chiorazzi N. B cell receptor signaling in chronic lymphocytic leukemia. Trends Immunol 2013; 34: 592-601).

The BCR is a multiprotein structure that is composed of an antigen binding subunit and a signaling subunit, which are non-covalently associated. The antigen-binding subunit consists of a membrane immunoglobulin containing two identical heavy chains and two identical light chains with one constant domain in each light chain and three in each heavy chain. Each heavy chain associates with a light chain to form an antigen-binding site. Each light and each heavy chain contains a variable domain forming the antigen-binding site. The immunoglobulin genes encoded in the Igh, Igl and Igk loci contain large numbers of V (variable), D (diversity) and J (joining) gene segments upstream of one or more constant exons. In a developing B cell, immunoglobulin gene rearrangement randomly assembles V, D and J gene segments to create a complete V exon in the Igh locus, and V and J gene segments in either the Igk or Igl locus. Through combinatorial joining of gene segments, junctional diversity and random heavy and light chain pairing, each individual B cell progenitor generates its own and nearly unique antigen binding subunit, whose antigen-binding affinity can be further refined by somatic hypermutation (SHM).

The BCR's signal transduction moiety is composed of a disulfide-linked heterodimer of the Igα and Igβ (CD79a/CD79b) proteins. Igα and Igβ each contain a single immunoreceptor tyrosine-based activation motif (ITAM) within their cytoplasmic tail that initiates signal transduction following BCR aggregation upon antigen-binding (Flaswinkel, H., Reth, M., 1994. Dual role of the tyrosine activation motif of the Ig-alpha protein during signal transduction via the B cell antigen receptor. EMBO J. 13, 83-89).

Antigen-binding rapidly activates the Src family kinase Lyn leading to the phosphorylation of Igα/Igβ. This initiates the formation of a large signaling complex on the cytoplasmic side of the membrane composed of the BCR, various tyrosine kinases, adaptor proteins, and signaling enzymes. Proximal BCR signaling is mediated by the protein tyrosine kinase Syk (spleen tyrosine kinase), which is recruited to the phosphorylated ITAMs of Igα and Igβ, leading to the propagation of the signal via association of Syk with the adaptor protein SLP65 and its downstream signaling enzymes Bruton's tyrosine kinase (BTK) and phospholipase Cγ2 (PLCγ2). Signals emanating the signaling complex activate downstream pathways, including calcium mobilization, phosphoinositide 3-kinases (PI3Ks), nuclear factor-κB (NF-κB), nuclear factor of activated T-cells (NF-AT), mitogen-activated protein kinases (MAPKs), and Rat sarcoma (RAS) signaling pathways (Burger J A and Chiorazzi N, 2013, s.a).

Chronic activation of mature B cells through the B-cell receptor has been shown to be a key process in the formation and development of CLL (Stevenson F K, Krysov S, Davies A J, Steele A J, Packham G. B-cell receptor signaling in chronic lymphocytic leukemia Blood. 2011; 118: 4313-4320). This agrees also with a study using EBV protein LMP2A as a constitutively active BCR surrogate, which showed that the development of a mouse B1 subset was dependent on a strong and prolonged BCR stimulation (Casola S, Otipoby K I, Alimzhanov M, et al. B cell receptor signal strength determines B cell fate. Nat Immunol 2004; 5: 317-27). Moreover, antigen-independent autonomous signalling of primary CLL B cells due to interactions of two neighbouring BCRs on a cell has been identified as a crucial driver of CLL development, resulting in elevated tyrosine phosphorylation of the BCR proximal signalling molecules, leading to periodic signalling and elevated Ca$^{2+}$ mobilization (Dührenvon Minden M et al. Chronic lymphocytic leukemia is driven by antigen-independent cell-autonomous signalling. Nature. 2012; 489: 309-313).

It is well documented that protein kinase Syk is constitutively phosphorylated through sustained BCR signaling, and several studies have revealed that also other key molecules of the signaling pathways downstream of BCR engagement in normal B cells, such as PKC, phosphoinositide 3-kinase and mitogen-activated protein kinase p38, are constitutively activated in B-CLL cells, resulting in the deregulation of the activity or expression of several prosurvival molecules and downstream pathways (Gobessi S, Laurenti L, Longo P G, Carsetti L, Berno V, Sica S et al. Inhibition of constitutive and BCR-induced Syk activation downregulates Mcl-1 and induces apoptosis in chronic lymphocytic leukemia B cells. *Leukemia* 2009; 23: 686-697. Ringshausen I, Schneller F, Bogner C, Hipp S, Duyster J, Peschel C et al. Constitutively activated phosphatidylinositol-3 kinase (PI-3K) is involved in the defect of apoptosis in B-CLL: association with protein kinase C delta. *Blood* 2002; 100: 3741-3748. Plate J M. PI3-kinase regulates survival of chronic lymphocytic leukemia B-cells by preventing caspase 8 activation. *Leuk Lymphoma* 2004; 45: 1519-1529. Sainz-Perez A, Gary-Gouy H, Portier A, Davi F, Merle-Beral H, Galanaud P et al. High Mda-7 expression promotes malignant cell survival and p38 MAP kinase activation in chronic lymphocytic leukemia. *Leukemia* 2006; 20: 498-504.).

Constitutively activated signaling pathways such as NF-kB or PI3K/AKT have been shown to lead to the transcription and overexpression of key antiapoptotic proteins, notably several members of the B-cell lymphoma 2 (Bcl-2) and inhibitor of apoptosis protein (IAP) families (Loeder S et al. A novel paradigm to trigger apoptosis in chronic lymphocytic leukemia. Cancer Res. 2009; 69: 8977-8986). It is well established that in addition to Bcl-2 itself, Mcl-1 is a crucial player in impaired apoptosis in CLL cells, and BCR signals reportedly upregulate Mcl-1 expression through the PI3K/AKT pathway (Petlickovski A, Laurenti L, Li X, Marietti S, Chiusolo P, Sica S, Leone G, Efremov D G. Sustained signaling through the B-cell receptor induces Mcl-1 and promotes survival of chronic lymphocytic leukemia B cells. Blood. 2005; 105: 4820-4827).

Different aspects of the BCR have been recognized to identify main CLL disease subtypes. For example, the level of somatic hypermutations within the variable region of the BCR immunoglobulin heavy chain (IGHV) has been used as a prognostic marker for decades. CLL patients with a mutated IGHV-gene (M-CLL), i.e. showing less than 98% IGHV gene identity with its closest germline, generally have a more indolent disease course than CLL patients with an unmutated IGHV gene with a germline identity equal to or above 98% (U-CLL). However, exceptions to this rule have been observed in which the mutational IGHV-gene status could not be correlated with a certain disease course. For example, cases using the IGHV3-21-gene, although mostly expressing a mutated BCR, had one of the worst clinical outcomes. A different approach, but also IGHV-determined, led to the categorization of around 30% of CLL cases into different prognostically important subsets, each with highly homogeneous biological features, clinical presentation and outcome. This categorization is based on the observation that, among mutated and unmutated cases, stereotyped BCRs carrying closely homologous heavy chain complementary determining region 3 (H-CDR3) sequences exist. Following this approach, the CLL cases characterized by the mutated IGHV3-21 could be assigned to the so-called Subset #2 (Stamatopoulos K, Belessi C, Moreno C, et al. Over 20% of patients with chronic lymphocytic leukemia carry stereotyped receptors: pathogenic implications and clinical correlations. Blood. 2007; 109(1): 259-270; Agathangelidis A., et al. Stereotyped B-cell receptors in one-third of chronic lymphocytic leukemia: A molecular classification with implications for targeted therapies. Blood. 2012; 119: 4467-4475).

Notably, the IGHV3-21 usage according to subset #2 has always been observed in association with the expression of an immunoglobulin lambda variable 3-21 chain along with an acquired substitution of glycine with arginine at amino acid position 110)(IGLV3-21$^{R110}$ in the light chain. Causative for the arginine 110 (R110) of IGLV3-21$^{R110}$ is a single G>C substitution on the splice site between the immunoglobulin lambda J and constant genes. The presence of R110 together with germline encoded lysine 16 (K16) in one BCR, and aspartates (D) 50 and 52 in a tyrosineaspartate-serine-aspartate (YDSD) motif of a neighbour BCR, has been identified to enable BCR-BCR interactions, thus triggering cell-autonomous signalling (FIGS. 6 and 7; Minici, C. et al., Distinct homotypic B-cell receptor interactions shape the outcome of chronic lymphocytic leukemia, Nature Comm. 2017; 8:15746).

In the course of epigenetic, genomic, and transcriptomic characterization of large cohorts of CLL patients focusing on the BCR light chain, it became clear that around 60% IGLV3-21$^{R110}$ cases carried non-stereotyped BCR, emphasizing that subset #2 is just a minor subgroup of CLL characterized by IGLV3-21$^{R110}$ (Stamatopoulos B, Smith T, Crompot E, et al. The Light Chain IgLV3-21 Defines a New Poor Prognostic Subgroup in Chronic Lymphocytic Leukemia: Results of a Multicenter Study. Clin Cancer Res. 2018; 24(20): 5048-5057. Nadeu F, Royo R, Clot G, et al. IGLV3-21$^{R110}$ identifies an aggressive biological subtype of chronic lymphocytic leukemia with intermediate epigenetics. Blood. 2021; 137(21): 2935-2946).

Of the 4 alleles of the IGLV3-21 gene which have been identified in humans, the alleles IGLV3-21*01 (IMGT/LIGM-DB accession No. X71966) and IGLV3-21*04 (IMGT/LIGM-DB accession No. AC279208) encode for the prerequisite K16 and D50 and D52, with the last two incorporated into a motif that, in most cases studied, included a tyrosine at position 49 and a serine at position 51 of IGLV3-21$^{R110}$ (for an exemplarily IGLV3-21$^{R110}$ see FIG. 7). However, functionally equivalent variations in this motif have also been observed in IGLV3-21$^{R110}$ CLL patients such as the replacement of the tyrosine with a phenylalanine or the serine with a threonine (Nadeu et al. 2021, s.a.;). Interestingly, the alleles IGLV3-21*01 and IGLV3-21*04 are strikingly underrepresented in B-cells of healthy donors, whereas all IGLV3-21 genes in patients studied by different groups could be assigned to allele IGLV3-21*01 or allele IGLV3-21*04 suggesting that these alleles might be mechanistically required for the development of the IGLV3-21$^{R110}$ associated CLL.

The IGLV3-21$^{R110}$ CLL subgroup, for which the name subset #2 L has also been proposed, is associated with a very aggressive disease course. Indeed, the poor outcome of the IGLV3-21$^{R110}$ CLL cases is independent of IGHV mutational status or the nature of the heavy chain. Since IGHV3-21$^{R110}$ is found in mutated CLL such as subset #2 (see above) as well as in association with different heavy chains such as IGHV1-18, IGHV3-53 or IGHV3-64 (Nadeu et al. 2021, supra), the IGLV3-21$^{R110}$ defines a group of CLL that is neither limited to the conventional subset classification based on empirically defined epigenetic stereotypes nor to the IGHV-mutational status. Moreover, the essential role of the R110 as a CLL driver mutation has been confirmed by site-specific mutagenesis experiments, which revealed that reversion of IGLV3-21$^{R110}$ into IGLV3-21$^{G110}$ resulted in abrogation of autonomous signalling capacity of the BCR (Stamatopoulos B, Smith T, Crompot E, et al. 2018, s.a.). Studies correlating time-to-first treatment (TTFT) and overall survival (OS) with the presence of IGLV3-21$^{R110}$-carrying BCR showed significant shorter values for patients expressing IGLV3-21$^{R110}$ compared to patients with non-IGLV3-21$^{R110}$ CLLs emphasizing a rapid need for therapy for IGLV3-21$^{R110}$-positive patients (Nadeu F et al. 2021; s.a.).

The CLL in these patients is usually treated with chemotherapeutics such as Idelalisip and Ibrutinib, both as single agents and in combination with other drugs. Idelalisip is an inhibitor of the hematopoetic cell restricted δ iso-form of PI3K, which promotes apoptosis in primary CLL cells (Hoellenriegel J, Meadows S A, Sivina M, et al. The phosphoinositide 3'-kinase delta inhibitor, CAL-101, inhibits B-cell receptor signaling and chemokine networks in chronic lymphocytic leukemia. Blood. 2011; 118: 3603-3612). Ibrutinib is an inhibitor of BTK that induces apoptosis in B-cell lymphomas and CLL-cells (Hermann S E, Gordon A L, Hertlein E, et al. Bruton tyrosine kinase represents a promising therapeutic target for treatment of chronic lymphocytic leukemia and is effectively targeted by PCI-32765. Blood. 2011; 117: 6287-6296). More recent therapies are increasingly using monoclonal antibodies such as e.g. Alemtuzumab, which acts as a CD52 antibody, or Obinutuzumab, Rituximab, and Ofatumumab, which target the cell surface B-linage-restricted antigen CD-20. By using these antibodies, the remission time can be extended by approximately 10 months. However, state-of-the-art therapies for the treatment are usually very stressful for the patient, since the drug targets are critical to the survival of both normal and malignant B cells, and low blood counts, including low levels of certain white blood cells (neutropenia), are common side effects. Moreover, with regard to chemotherapeutics, a high infection risk, latent infections and off-target effects to immune system have been reported as further side effects. In general it can be summarized that the undesired side effects of the therapy and the often insufficient effect of the drugs lead to a high death rate, because not only tumor cells, but also healthy cells of the immune system are damaged.

From that, a specific treatment option for IGLV3-21$^{R110}$-positive CLL patients that does not come along with the aforementioned side effects, still remains to be found.

Current investigations regarding potential antibodies targeting IGLV3-21$^{R110}$ harboring BCRs mainly focus on diagnosis of this specific subtype of CLL. As a matter of example, Maity et al. describe immunophenotyping studies with an anti IGLV3-21$^{R110}$ antibody that is used as prognostic marker for CLL. Said diagnostic anti-IGLV3-21$^{R110}$ antibody is disclosed to be a IgG2a and Igκ antibody (Maity P C, Bilal M, Koning M T, et al. IGLV3-21*01 is an inherited risk factor for CLL through the acquisition of a single-point mutation enabling autonomous BCR signalling. PNAS. 2020; 117(8): 4320-4327).

A first step forward towards opening up a treatment option is disclosed in WO 2019/008129, which discloses antibodies that can be used to remove CLL cells from blood samples. The antibodies of WO 2019/008129 have been expressed as IgG antibodies in a hybridoma cell line departing from a murine host. WO 2019/008129 discloses the respective variable heavy- and light-chain domains of such antibodies only.

WO 2019/008129 does not show that the antibodies disclosed therein are selective between healthy and diseased tissues nor that they have been applied in vivo. Thus any therapeutic effect thereof is not shown.

From the foregoing, a treatment option, particularly an antibody that is specific, selective and non-cross-reactive to other tissues, which would allow an improved treatment of CLL in IGLV3-21$^{R110}$ positive patients is still unknown, but required.

SUMMARY OF THE INVENTION

The present invention solves the above problem, by providing in a first aspect an antibody having a heavy chain amino acid sequence of SEQ ID NO: 1 and a light chain amino acid sequence of SEQ ID NO: 2, or a heavy chain amino acid sequence of SEQ ID NO: 11 and a light chain amino acid sequence of SEQ ID NO: 12; or an antibody comprising a variable heavy chain having a sequence selected from the list consisting of SEQ ID NO: 15 and SEQ ID NO: 20 in any combination with a variable light chain having a sequence selected from the list of SEQ ID NO: 16, SEQ ID NO: 17, SEQ ID NO: 18, and SEQ ID NO: 19.

Such antibody specifically, selectively and non-cross-reactive with other tissues of the CLL patient binds to the IGLV3-21$^{R110}$-harboring BCR and thereby kills malignant B-cells. While recognizing the presence of the IGLV3-21$^{R110}$-part of the BCR, this new antibody is also capable of treating "subset #2 CLL", which is characterized by BCR's comprising an IGHV3-21/IGLV3-21$^{R110}$-combination or any other CLL comprising IGLV3-21$^{R110}$.

The provision of these antibodies results in a second aspect of the present invention, which is the provision of said antibodies for use in the treatment of CLL in IGLV3-21$^{R110}$ positive patients. Likewise this second aspect of the present invention pertains to a method of treatment of CLL in IGLV3-21$^{R110}$ positive patients, by administering a therapeutically active amount of said antibodies.

This is the first treatment option for CLL in IGLV3-21$^{R110}$ positive patients, which enables selective killing of malignant B-cells without the side-effects that are associated with treatments offered by the state of the art. Even more so, the binding and killing of B-cells that are only characterized by the presence of an IGLV3-21$^{R110}$-harboring BCR that was identified as a marker for CLL, makes such treatment independent of the requirement of such CLL to belong of any of the previously identified subsets of CLL that are defined by a certain IGHV.

Without being bound to a theory, the treatment with the antibodies of the present invention, is deemed to induce a hyper-activation of B-cells via the IGLV3-21$^{R110}$ of the BCR in absence of a co-stimulatory signal. This finally results in the induction of apoptosis in the CLL cells bound by the antibodies. Therefore the treatment with the antibodies of the present invention is highly selective for malignant B-cells and amongst those even more selective for IGLV3-21$^{R110}$ positive B-cells.

In a third aspect the invention is also related to DNA molecules (nucleic acids) encoding the antibodies of the invention. Thus, the invention also relates to vectors and host cells containing a nucleic acid sequence of the invention.

Definitions

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent the meaning commonly understood in the art. Such references include, but are not limited to, Singleton et ah, Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W. B. Saunders Company. Any additional technical resources available to the person of ordinary skill in the art providing definitions of terms used herein having the meaning commonly understood in the art can be consulted. For the purposes of the present invention, the following terms are further defined.

As used herein and in the appended claims, the singular forms "a," "and," and "the" include plural reference unless the context clearly dictates otherwise. Thus, for example, reference to "a gene" is a reference to one or more genes and includes equivalents there of known to those skilled in the art, and so forth.

An "autonomously active" BCR is a special type of a permanently active BCR. While the conventional activation is based on an external antigen, the autonomously active BCR results from its interaction with membrane structures on the surface of the same cell. For the clinical picture of CLL, an autonomic activation-triggering interaction between BCRs adjacent to each other on the surface of the same cell could be shown (e.g. M. Dühren-von Minden et. al; Nature 2012).

IGLV3-21$^{R110}$ is the light chain variable region of the BCR, that enables BCR-BCR interactions, to induce an autonomously active BCR. Structurally such IGLV3-21$^{R110}$ is characterized by a sequence identity of more than 80% to the sequence as represented by SEQ ID NO 53, wherein in any case at position 110 of said sequence there is Arginine and not Glycin.

The term "antibody", as used herein, is intended to refer to immunoglobulin molecules. Preferably comprised of four polypeptide chains, two heavy (H) chains and two light (L) chains which are typically inter-connected by disulfide bonds. Each heavy chain is comprised of a heavy chain variable region (abbreviated herein as VH) and a heavy chain constant region. The heavy chain constant region can comprise e.g. three domains CHL CH2 and CH3. Each light chain is comprised of a light chain variable region (abbreviated herein as VL) and a light chain constant region. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs. arranged from amino terminus to carboxy-terminus e.g. in the following order: FR1, CDR1, FR2, CDR2, FR3, CDR3, FR4.

As used herein, the term "Complementarity Determining Regions (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Chothia and Lesk (J Mol Biol 196: 901-917 (1987)), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). Each complementarity determining region comprises amino acid residues as defined by IMGT. In some instances, a complementarity determining region can also include amino acids from a CDR region defined according to Kabat and/or a hypervariable loop according to Chothia numbering system.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA, and IgA2. The heavy-chain constant domains that correspond to the different classes of antibodies are called [alpha], [delta], [epsilon], [gamma], and [mu], respectively. The subunit structures and three-dimensional configurations of different classes of immunoglobulins are well known.

As used herein the term "antibody" is understood to also include antigen-binding fragments and variants thereof. Thus, any reference to "antibody" in the context of the present invention is also a reference to an antigen-binding fragment and/or variant thereof, if not expressively stated otherwise, such as by specifying a full heavy or full light chain of an antibody that are combined to form said antibody.

An "antigen-binding fragment" hereby is defined as a fragment of an antibody/immunoglobulin (e.g., a variable region of an IgG) that retains the antigen-binding region. Antigen-binding fragments of the invention include Fab, Fab', F(ab')$_2$, and Fv fragments; diabodies; single domain antibodies (DAbs), linear antibodies; single-chain antibody molecules (scFv); and multispecific, such as bi- and tri-specific, antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "multi-specific" or "multi-functional" antibody is understood to have each of its binding sites identical. The F(ab')2 or Fab may be engineered to minimize or completely remove the intermolecular disulphide interactions that occur between the CH1 and CL domains.

An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs.

A "variant" of an antibody or antigen-binding fragment contemplated in the invention is a molecule in which the binding activity of the antibody or antigen-binding fragment for IGLV3-21$^{R110}$ is maintained.

A "humanized" antibody is defined herein as one that is (i) derived from a non-human source (e.g., a transgenic mouse which bears a heterologous immune system), which antibody is based on a human germline sequence; (ii) where amino acids of the framework regions of a non-human antibody are partially exchanged to human amino acid sequences by genetic engineering or (iii) CDR-grafted, wherein the CDRs of the variable domain are from a non-human origin, while one or more frameworks of the variable domain are of human origin and the constant domain (if any) is of human origin.

A "chimeric" antibody is defined herein as one, wherein the variable domains are derived from a non-human origin and some or all constant domains are derived from a human origin.

The term "monoclonal" antibody as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. The term monoclonal antibody specifically includes murine, chimeric and humanized antibodies.

As used herein, an antibody "binds specifically to", is "specific to/for" or "specifically recognizes" an antigen of interest, e.g. a tumor-associated polypeptide antigen target (here, IGLV3-21$^{R110}$, is able to discriminate between such antigen and one or more reference antigen(s). In its most general form, "specific binding". "binds specifically to", is "specific to/for" or "specifically recognizes" is referring to the ability of the antibody to discriminate between the antigen of interest and an unrelated antigen, as determined, for example, in accordance with one of the following methods. Such methods comprise, but are not limited to Flow cytometry, Western blots, ELISA-, RIA-, ECL-, IRMA-, immunohistological-tests and peptide scans.

"Binding affinity" or "Affinity" refers to the strength of the sum total of noncovalent interactions between a single binding site of a molecule and its binding partner. Unless indicated otherwise, as used herein, "binding affinity" or "Affinity" refers to intrinsic binding affinity which reflects a 1:1 interaction between members of a binding pair (e.g. an antibody and an antigen). Dissociation rate constant $K_D$ are usually calculated based on the ratio of equilibrium association ($k_a$) and dissociation rate ($k_d$) constants. The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. The term "high affinity" means, that the antibody binds to IGLV3-21$^{R110}$-positive CLL BCR with an affinity ($K_D$) of lower than or equal to $10^{-9}$ M (monovalent affinity). The antibody may have substantially greater affinity for the target antigen compared to other unrelated molecules. Affinity can be measured by common methods known in the art, e.g. according to Example 5.

As used herein, the term 'epitope' includes any protein determinant capable of specific binding to an immunoglobulin or T-cell receptors. Epitopic determinants usually consist of chemically active surface groupings of molecules such as amino acids or sugar side chains, or combinations thereof and usually have specific three dimensional structural characteristics, as well as specific charge characteristics.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or nonproteinaceous solutes. In preferred embodiments, the antibody is purified (1) to greater than 95% by weight of antibody as determined e.g. by the Lowry method, IN-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

The term "cancer" refers to the physiological condition or disease in which cells divide without control leading to unregulated cell growth. A "tumor" comprises one or more cancer cells.

"Antibody-dependent cell-mediated cytotoxicity" or "ADCC" refers to a form of cytotoxicity in which secreted Ig bound onto Fc gamma receptors (FcγRs) present on certain cytotoxic cells (e.g. NK cells, neutrophils, and macrophages) enable these cytotoxic effector cells to bind specifically to an antigen-bearing target cell and subsequently kill the target cell e.g. with cytotoxins.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202: 163 (1996), may be performed. Polypeptide variants with altered Fc region amino acid sequences (polypeptides with a variant Fc region) and increased or decreased C1q binding are described, e.g., in U.S. Pat. No. 6,194,551 BI and WO 1999/51642.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN, LALIGN or Megalign (DNASTAR) software. Those skilled in the art can determine appropriate parameters for aligning sequences, including any algorithms needed to achieve maximal alignment over the full length of the sequences being compared.

DETAILED DESCRIPTION OF THE INVENTION

First Aspect-of the Invention—Antibodies

The antibodies of the present invention are based on the discovery of a novel murine antibody that has a specific affinity for BCRs harboring IGLV3-21$^{R110}$ and that can deliver a therapeutic benefit to a subject. The antibodies and their beneficial properties enabling therapeutic activity are described in more detail hereinafter.

The antibodies of the invention, which may be murine, humanized or chimeric, can be used in many contexts, which are more fully described herein.

According to the first aspect of the present invention, antibodies having a heavy chain amino acid sequence of SEQ ID NO: 1 and a light chain amino acid sequence of SEQ ID NO: 2, or a heavy chain amino acid sequence of SEQ ID NO: 11 and a light chain amino acid sequence of SEQ ID NO: 12; or antibodies comprising a variable heavy chain having a sequence selected from the list consisting of SEQ ID NO: 15 and SEQ ID NO: 20 in any combination with a variable light chain having a sequence selected from the list of SEQ ID NO: 16, SEQ ID NO: 17, SEQ ID NO: 18, and SEQ ID NO: 19 are provided.

These antibodies can be murine, humanized or chimeric antibodies and they specifically bind to the IGLV3-21$^{R110}$-BCR with high affinity.

As outlined above, it is believed that these antibodies strongly activate the IGLV3-21$^{R110}$-BCR. More specifically these antibodies lead to a strong phosphorylation of Syk, BTK, and PI3K on the short term, which induces apoptosis and thus finally inhibits tumor growth in vivo.

Preferred embodiments of the first aspect of the present invention are further characterized in more detail in Table 1 and Table 2 of the Examples.

The antibody "mAb01-01" is therefore a first preferred embodiment of the first aspect of the present invention, which is characterized by a heavy chain corresponding to SEQ ID NO: 1 and a light chain corresponding to SEQ ID NO: 2.

The antibody "HC0-LC0" is therefore a second preferred embodiment of the first aspect of the present invention, which is characterized by a heavy chain corresponding to SEQ ID NO: 11 and a light chain corresponding to SEQ ID NO: 12.

The antibody "HC6-LC6" is therefore a third preferred embodiment of the first aspect of the present invention, which is characterized by a variable heavy chain region corresponding to SEQ ID NO: 15 and a variable light chain region corresponding to SEQ ID NO: 16.

Within said third preferred embodiment of the first aspect of the invention, an antibody characterized by a heavy chain corresponding to SEQ ID NO: 13 and a light chain corresponding to SEQ ID NO: 14 is more preferred.

The antibody "HC6-LC7" is therefore a fourth preferred embodiment of the first aspect of the present invention, which is characterized by a variable heavy chain region corresponding to SEQ ID NO: 15 and a variable light chain region corresponding to SEQ ID NO: 17.

Within said fourth preferred embodiment of the first aspect of the invention, an antibody characterized by a heavy chain corresponding to SEQ ID NO: 13 and a light chain corresponding to SEQ ID NO: 22 is more preferred.

The antibody "HC6-LC8" is therefore a fifth preferred embodiment of the first aspect of the present invention, which is characterized by a variable heavy chain region corresponding to SEQ ID NO: 15 and a variable light chain region corresponding to SEQ ID NO: 18.

Within said fifth preferred embodiment of the first aspect of the invention, an antibody characterized by a heavy chain corresponding to SEQ ID NO: 13 and a light chain corresponding to SEQ ID NO: 23 is more preferred.

The antibody "HC6-LC9" is therefore a sixth preferred embodiment of the first aspect of the present invention, which is characterized by a variable heavy chain region corresponding to SEQ ID NO: 15 and a variable light chain region corresponding to SEQ ID NO: 19.

Within said sixth preferred embodiment of the first aspect of the invention, an antibody characterized by a heavy chain corresponding to SEQ ID NO: 13 and a light chain corresponding to SEQ ID NO: 24 is more preferred.

The antibody "HC7-LC6" is therefore a seventh preferred embodiment of the first aspect of the present invention, which is characterized by a variable heavy chain region corresponding to SEQ ID NO: 20 and a variable light chain region corresponding to SEQ ID NO: 16.

Within said seventh preferred embodiment of the first aspect of the invention, an antibody characterized by a heavy chain corresponding to SEQ ID NO: 21 and a light chain corresponding to SEQ ID NO: 14 is more preferred.

The antibody "HC7-LC7" is therefore an eighth preferred embodiment of the first aspect of the present invention, which is characterized by a variable heavy chain region corresponding to SEQ ID NO: 20 and a variable light chain region corresponding to SEQ ID NO: 17.

Within said eighth preferred embodiment of the first aspect of the invention, an antibody characterized by a heavy chain corresponding to SEQ ID NO: 21 and a light chain corresponding to SEQ ID NO: 22 is more preferred.

The antibody "HC7-LC8" is therefore a ninth preferred embodiment of the first aspect of the present invention, which is characterized by a variable heavy chain region corresponding to SEQ ID NO: 20 and a variable light chain region corresponding to SEQ ID NO: 18.

Within said ninth preferred embodiment of the first aspect of the invention, an antibody characterized by a heavy chain corresponding to SEQ ID NO: 21 and a light chain corresponding to SEQ ID NO: 23 is more preferred.

The antibody "HC7-LC9" is therefore a tenth preferred embodiment of the first aspect of the present invention, which is characterized by a variable heavy chain region corresponding to SEQ ID NO: 20 and a variable light chain region corresponding to SEQ ID NO: 19.

Within said tenth preferred embodiment of the first aspect of the invention, an antibody characterized by a heavy chain corresponding to SEQ ID NO: 21 and a light chain corresponding to SEQ ID NO: 24 is more preferred.

Antibodies of this first aspect of the invention are not limited to the specific peptide sequences provided. Rather, the invention also embodies variants. With reference to the instant disclosure and conventionally available technologies and references, the skilled worker will be able to prepare, test and utilize functional variants of the antibodies disclosed herein, while appreciating these variants having the ability to bind to the IGLV3-21$^{R110}$-BCR and thereby killing the B-cell fall within the scope of the present invention.

A variant can include, for example, an antibody that has at least one altered complementary determining region (CDR) (hyper-variable) and/or framework (FR) (variable) domain/position, vis-a-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs (complementarity determining regions). The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences.

As a matter of example, the skilled worker can use the sequences of the antibodies provided herein (e.g. of Table 1 and/or Table 2) to design peptide variants that are within the scope of the present invention.

Furthermore, variants may be obtained by using one antibody of this first aspect of the invention as starting point for optimization by diversifying one or more amino acid residues in the antibody, preferably amino acid residues in one or more CDRs, and by screening the resulting collection of antibody variants. Diversification can be done by synthesizing a collection of DNA molecules using trinucleotide mutagenesis (TRIM) technology (Virnekiis B. et al., Nucl. Acids Res. 1994, 22: 5600.). Antibodies include molecules with modifications/variations including but not limited to e.g. modifications leading to altered half-life (e.g. modification of the Fe part or attachment of further molecules such as PEG), altered binding affinity or altered ADCC or CDC activity.

Polypeptide variants may be made that conserve the overall molecular structure of an antibody peptide sequence described herein. Given the properties of the individual amino acids, some rational substitutions will be recognized by the skilled worker. Amino acid substitutions, "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, praline, phenylalanine, tryptophane, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and praline may be substituted for one another based on their ability to disrupt a-helices. Similarly, certain amino acids, such as alanine, cysteine, leucine, methionine, glutamic acid, glutamine, histidine and lysine are more commonly found in a-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

The third to tenth preferred embodiments of the antibodies pursuant to the first aspect of the present invention may also comprise a variable heavy chain which is at least 83.3%, 85%, 90%, 92%, 95% sequence identical to the variable heavy chain as presented by SEQ ID NO: 15, or at least 82.5%, 85%, 90%, 92%, 95% sequence identical to the variable heavy chain as presented by SEQ ID NO: 20.

The third to tenth preferred embodiments of the antibodies pursuant to the first aspect of the present invention may also comprise a variable light chain which is at least 90%, 92%, 95% sequence identical to the variable light chain as presented by SEQ ID NO: 16, or at least 87%, 90%, 92%, 95% identical to the variable light chain as presented by SEQ ID NO: 17, or at least 80.5%, 85%, 90%, 92%, 95% sequence identical to the variable light chain as presented by SEQ ID NO: 18, or at least 77.7%, 80%, 85%, 90%, 92%, 95% sequence identical to the variable light chain as presented by SEQ ID NO: 19.

All of the preferred embodiments of the antibodies pursuant to the first aspect of the present invention combine a variable heavy chain sequence comprising sequences as represented by SEQ ID NO: 5 (H-CDR 1), SEQ ID NO: 6 (H-CDR 2) and SEQ ID NO: 7 (H-CDR 3) with a variable light chain sequence comprising sequences as represented by SEQ ID NO: 8 (L-CDR 1), SEQ ID NO: 9 (L-CDR 2), SEQ ID NO: 10 (L-CDR 3).

The antibodies pursuant to the first aspect of the invention are preferably an IgG of any isotype (e.g., $IgG_1$ $IgG_2$, $IgG_3$, $IgG_4$). Their respective antigen-binding fragments may be a Fab, Fab', F(ab')2 or scFv, for example.

More preferably, the antibodies pursuant to the first aspect of the present invention are expressed as $IgG_1$ isotype antibodies and are even more preferably humanized.

The most preferred antibodies of the first aspect of the present invention are those of the second, third and seventh embodiment ("HC0-LC0", "HC6-LC6" and "HC7-LC6"), wherein amongst those the foremost preferred antibodies are those of the third and seventh embodiment ("HC6-LC6" and "HC7-LC6").

All of the aforesaid preferred embodiments of the first aspect of the present invention are particularly advantageous, as they have been shown to display a very high affinity in the range of $K_D$~$10^{-10}$ M, resulting in beneficial aspect of the present invention that they specifically, selectively and non-cross-reactive with other tissues of the CLL patient bind to the IGLV3-21$^{R110}$-harboring BCR and thereby enable selective killing of malignant B-cells.

Regarding the most preferred antibodies ("HCO-LC0", "HC6-LC6" and "HC7-LC6"), those display the highest affinity of only about between 1.2 to 2.1 10-10 M. The antibodies "HC6-LC6" and "HC7-LC6" according to the third and seventh preferred embodiment are additionally humanized, rendering them particularly suitable for therapeutic use due to their reduced immunogenicity.

All of the aforementioned embodiments of the first aspect of the invention selectively bind to IGLV3-21$^{R110}$. Beyond the definition provided for IGLV3-21$^{R110}$ above, said IGLV3-21$^{R110}$ is in a generally preferred embodiment of this first aspect of the invention further characterized by a sequence identity of more than 80% to the sequence as represented by SEQ ID NO 53, wherein at position 16 of said sequence there is lysine and at positions 50 and 52 there are aspartates. In a generally more preferred embodiment of this first aspect of the invention, at position 49 there is a tyrosine or a phenylalanine and at position 51 there is a serine or a threonine. In a generally further more preferred embodiment of this first aspect of the invention at position 49 there is a tyrosine and at position 51 there is a serine.

Second Aspect of the Invention—Therapeutic Use

The second aspect of the present invention, pertains to the provision of the antibodies of the first aspect of the present invention for use in the treatment of CLL in IGLV3-21$^{R110}$ positive patients. Likewise this second aspect of the present invention pertains to a method of treatment of CLL in IGLV3-21$^{R110}$ positive patients, by administering a therapeutically active amount of antibodies of the first aspect of the present invention.

In a first preferred embodiment of this second aspect of the present invention, the antibodies are therefore characterized by a heavy chain corresponding to SEQ ID NO: 1 and a light chain corresponding to SEQ ID NO: 2.

In a second preferred embodiment of this second aspect of the present invention, the antibodies are characterized by a heavy chain corresponding to SEQ ID NO: 11 and a light chain corresponding to SEQ ID NO: 12.

In a third preferred embodiment of this second aspect of the present invention, the antibodies are characterized by a variable heavy chain region corresponding to SEQ ID NO: 15 and a variable light chain region corresponding to SEQ ID NO: 16.

Within said third preferred embodiment, antibodies characterized by a heavy chain corresponding to SEQ ID NO: 13 and a light chain corresponding to SEQ ID NO: 14 are more preferred.

In a fourth preferred embodiment of this second aspect of the present invention, the antibodies are characterized by a variable heavy chain region corresponding to SEQ ID NO: 15 and a variable light chain region corresponding to SEQ ID NO: 17.

Within said fourth preferred embodiment, antibodies characterized by a heavy chain corresponding to SEQ ID NO: 13 and a light chain corresponding to SEQ ID NO: 22 are more preferred.

In a fifth preferred embodiment of this second aspect of the present invention, the antibodies are characterized by a variable heavy chain region corresponding to SEQ ID NO: 15 and a variable light chain region corresponding to SEQ ID NO: 18.

Within said fifth preferred embodiment, antibodies characterized by a heavy chain corresponding to SEQ ID NO: 13 and a light chain corresponding to SEQ ID NO: 23 are more preferred.

In a sixth preferred embodiment of this second aspect of the present invention, the antibodies are characterized by a variable heavy chain region corresponding to SEQ ID NO: 15 and a variable light chain region corresponding to SEQ ID NO: 19.

Within said sixth preferred embodiment, antibodies characterized by a heavy chain corresponding to SEQ ID NO: 13 and a light chain corresponding to SEQ ID NO: 24 are more preferred.

In a seventh preferred embodiment of this second aspect of the present invention, the antibodies are characterized by a variable heavy chain region corresponding to SEQ ID NO: 20 and a variable light chain region corresponding to SEQ ID NO: 16.

Within said seventh preferred embodiment, antibodies characterized by a heavy chain corresponding to SEQ ID NO: 21 and a light chain corresponding to SEQ ID NO: 14 are more preferred.

In an eighth preferred embodiment of this second aspect of the present invention, the antibodies are characterized by a variable heavy chain region corresponding to SEQ ID NO: 20 and a variable light chain region corresponding to SEQ ID NO: 17.

Within said eighth preferred embodiment, antibodies characterized by a heavy chain corresponding to SEQ ID NO: 21 and a light chain corresponding to SEQ ID NO: 22 are more preferred.

In a ninth preferred embodiment of this second aspect of the present invention, the antibodies are characterized by a variable heavy chain region corresponding to SEQ ID NO: 20 and a variable light chain region corresponding to SEQ ID NO: 18.

Within said ninth preferred embodiment, antibodies characterized by a heavy chain corresponding to SEQ ID NO: 21 and a light chain corresponding to SEQ ID NO: 23 are more preferred.

In a tenth preferred embodiment of this second aspect of the present invention, the antibodies are characterized by a variable heavy chain region corresponding to SEQ ID NO: 20 and a variable light chain region corresponding to SEQ ID NO: 19.

Within said tenth preferred embodiment, antibodies characterized by a heavy chain corresponding to SEQ ID NO: 21 and a light chain corresponding to SEQ ID NO: 24 are more preferred.

As mentioned in the context of the first aspect of the present invention, all of the above referred to embodiments of the second aspect of the invention rely on antibodies that have a very high affinity. None thereof has an affinity of more than about $3 \cdot 10^{-10}$ M at a capture rate of about 0.3 nm. From that alone the second aspect of the present invention allows a highly selective treatment of CLL in patients that are IGLV3-21$^{R110}$ positive.

It has now further been demonstrated that these antibodies (see FIG. 1) may selectively discriminate between the wild-type IGLV3-21$^{G110}$ variant and the malignant IGLV3-21$^{R110}$ variant and that treatment with these antibodies in a xenograft mouse model (see FIG. 5 and Example 9) results in significant depletion of human IGLV3-21$^{R110}$-positive B-cells, resulting in amelioration of CLL.

It has therefore been surprisingly found that the antibodies for use in the treatment of CLL in IGLV3-21$^{R110}$-positive patients is efficacious.

Furthermore it could be shown that antibodies used for such treatment do not display cross-reactivity to other tissues (see FIG. 4, Example 8).

The determination of an effective dose of such antibodies is well within the capability of those skilled in the art. For any compound, the therapeutically effective dose can be estimated initially either in cell culture assays, e.g., neoplastic cells, or in animal models, usually mice, rabbits, dogs, pigs or monkeys. The animal model is also used to achieve a desirable concentration range and route of administration. Such information can then be used to determine useful doses and routes for administration in humans.

A therapeutically effective dose refers to that amount of an antibody that ameliorates the symptoms or condition to be treated. In the context of the present invention, such condition to be treated is a clinically manifest CLL, which is caused by aberrant proliferation of B-cells that have an autonomously active BCR. More specifically the second aspect of the present invention addresses a clinically manifest CLL which is characterized by an aberrant proliferation of B-cells that have an autonomously active BCR harboring IGLV3-21$^{R110}$.

All of the aforementioned embodiments of the second aspect of the invention pertain to the treatment of CLL in patients that are IGLV3-21$^{R110}$ positive. Beyond the definition provided for IGLV3-21$^{R110}$ above, said IGLV3-21$^{R110}$ is in a generally preferred embodiment of this second aspect of the invention further characterized by a sequence identity of more than 80% to the sequence as represented by SEQ ID NO 53, wherein at position 16 of said sequence there is lysine and at positions 50 and 52 there are aspartates. In a generally more preferred embodiment of this first aspect of the invention, at position 49 there is a tyrosine or a phenylalanine and at position 51 there is a serine or a threonine. In a generally further more preferred embodiment of this first aspect of the invention at position 49 there is a tyrosine and at position 51 there is a serine.

A therapeutically effective amount is therefore an amount of an antibody that is of sufficient quantity to deplete IGLV3-21$^{R110}$-positive CLL cells in a treated area of a patient—either as a single dose or according to a multiple dose regimen, yet which amount is toxicologically tolerable.

In the second aspect of the invention antibodies for the use in the treatment of CLL in IGLV3-21$^{R110}$ positive patients are preferred that are employed at a dose from 0.25 to 25 mg/kg$_{bodyweight}$, more preferably from 1 to 20 mg/kg$_{bodyweight}$, most preferably from more than 7 to 15 mg/kg$_{bodyweight}$ and especially preferable from 8 to 12 mg/kg$_{bodyweight}$.

These dosages are extremely low, resulting in an overall drug amount to be hypothetically administered to an average human patient of about 80 kg of no more than especially preferable between 640 to 960 mg to achieve strong depletion of malignant B-cells.

The exact dosage is chosen by the individual physician in view of the patient to be treated. Dosage and administration are adjusted to provide sufficient levels of the active moiety or to achieve the desired effect. It has however been shown by the present invention that a twice weekly dosage of no more than 0.3 mg/kg is already efficacious in a xenograft mouse model, while strong depletion of malignant cells could be achieved at a dosage of 10 mg/kg (twice weekly).

When dosing the antibodies pursuant to the second aspect of the present invention, additional factors may also be taken into account, which may include the severity of the disease state, e.g., tumor size and location; age, weight and gender of the patient and diet. Further influencing factors to determine an adequate dose may be drug combination(s), reaction sensitivities, and tolerance/response to therapy.

Furthermore, the dosing may be performed more than once and time and frequency of administration may further influence the individual dosage administered.

Pursuant to the second aspect of the present invention, the antibodies may also be co-administered with known medicaments. Therefore they may be administered as the sole pharmaceutical agent or in combination with one or more additional therapeutic agents where the combination causes no unacceptable adverse effects. This combination therapy includes administration of a single pharmaceutical dosage formulation which contains antibodies pursuant to the first aspect of the invention and one or more additional therapeutic agents, as well as administration of an antibody of the first aspect of the invention and each additional therapeutic agent in its own separate pharmaceutical dosage formulation.

Where separate dosage formulations are used, treatment pursuant to the second aspect of this invention with one or more additional therapeutic agents may be at essentially the same time (e.g., concurrently) or at separately staggered times (e.g., sequentially). In particular, the treatment pursuant to the present invention may be performed in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, antiangiogenic compounds, and other anti-tumor drugs.

The antibodies of the present invention may also be employed in cancer treatment in conjunction with radiation therapy and/or surgical intervention.

Third Aspect—Polynucleotides

The present invention also relates to the DNA molecules that encode an antibody of the first aspect of the invention.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook, J., Fritsch, E. F. and Maniatis, T. (1989) Molecular Cloning: A laboratory manual, Cold Spring Harbor Laboratory Press, Cold Spring Harbor, USA and Ausubel et al., 1995 (Ausubel, F. M., Brent, R., Kingston, R. E., Moore, D. D., Sedman, J. G., Smith, J. A., & S1ruhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where Tm is the melting temperature of a nucleic acid duplex):

a. $T_m = 69.3 + 0.41$ (G+C) %
b. The Tm of a duplex DNA decreases by 1° C. with every increase of 1% in the number of mismatched base pairs.
c. $(T_m)\mu 2 - (T_m)\mu 1 = 18.5 \log_{10} \mu 2/\mu 1$
 where p1 and p2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Yet another class of DNA variants within the scope of the invention may be described with reference to the product they encode. These functionally equivalent polynucleotides are characterized by the fact that they encode the same peptide sequences found in SEQ ID NOS: 1 to 24 due to the degeneracy of the genetic code.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

As with the first aspect of the present invention, there are also corresponding preferred embodiments of this third aspect of the invention.

In a first preferred embodiment of this third aspect of the present invention, this invention pertains to DNA molecules encoding a heavy chain of one the preferred antibodies of the first aspect of the present invention as represented by any sequence selected from the list consisting of SEQ ID NO: 25, SEQ ID NO: 29, SEQ ID NO: 33 and SEQ ID NO: 38.

In a second preferred embodiment of this third aspect of the present invention, this invention pertains to DNA molecules encoding a light chain of one the preferred antibodies of the first aspect of the present invention as represented by any sequence selected from the list consisting of SEQ ID NO: 26, SEQ ID NO: 30, SEQ ID NO: 34, SEQ ID NO: 35, SEQ ID NO: 36 and SEQ ID NO: 37.

Nucleic acids of the invention are suitable for recombinant production of antibodies using standard vectors and host cells containing a nucleic acid sequence of the invention.

Further Aspects of the Invention

The antibodies of the first aspect of the present invention that are used in the second aspect of the present invention may be co-administered with known medicaments. For example, the antibody might be co-administered with any general anti-B-cell antibodies.

The present invention also relates to compositions comprising the antibodies according to any of the embodiments of the first aspect of the invention, which may be used analogously to the second aspect of the invention.

The invention, therefore, includes a pharmaceutical composition comprising an antibody pursuant to the first aspect of the invention alone or in combination with at least one other agent and a pharmaceutically acceptable carrier or excipient.

The other agent may be for instance a stabilizing compound and such at least one other agent and the antibody according to the first aspect of the invention may be administered in any sterile, biocompatible pharmaceutical carrier, including, but not limited to, saline, buffered saline, dextrose, and water.

The pharmaceutical compositions of the present invention may be manufactured in a manner that is known in the art, e.g., by means of conventional mixing, dissolving, emulsifying, encapsulating, entrapping or lyophilizing processes.

A preferred pharmaceutical composition is made up from a lyophilized powder of the antibody according to the first aspect of the invention in 1 mM-50 mM histidine, 0.1%-2% sucrose, 2%-7% mannitol at a pH range of 4.5 to 5.5 that is combined with buffer prior to use.

After pharmaceutical compositions comprising an antibody of the invention formulated in an acceptable carrier have been prepared, they can be placed in an appropriate container and labeled for treatment of an indicated condition.

Consequentially, in a related aspect, the present invention also relates to such pharmaceutical compositions for use of CLL in IGLV3-21$^{R110}$ positive patients. Likewise this related aspect of the present invention pertains to a method of treatment of CLL in IGLV3-21$^{R110}$ positive patients, by administering a therapeutically active amount of said such pharmaceutical compositions.

Such administration is usually accomplished parenterally. Methods of parenteral delivery include topical, intra-arterial (directly to the tumor), intramuscular, subcutaneous, intramedullary, intrathecal, intraventricular, intravenous, intraperitoneal, or intranasal administration.

The preferred routes of administration are intravenous and intra-arterial (directly to the tumor).

Pharmaceutical compositions for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

In another embodiment, the kits may contain DNA sequences encoding the antibodies pursuant to the third aspect of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmid may also contain numerous other elements to facilitate cloning and expression of the encoded proteins. Such elements are well known to those of skill in the art and include, for example, selectable markers, initiation codons, termination codons, and the like.

The invention therefore further relates to the aforementioned packs and kits comprising one or more containers filled with one or more of the ingredients of the aforementioned compositions of the invention for use in the treatment of CLL in IGLV3-21$^{R110}$ positive patients.

A preferred embodiment of the invention is:
A. Antibodies for use in the treatment of CLL in IGLV3-21$^{R110}$ positive patients, wherein said antibodies have
a heavy chain amino acid sequence of SEQ ID NO: 1 and a light chain amino acid sequence of SEQ ID NO: 2; or
a heavy chain amino acid sequence of SEQ ID NO: 11 and a light chain amino acid sequence of SEQ ID NO: 12; or comprise a
- variable heavy chain having a sequence selected from the list consisting of SEQ ID NO: 15 and SEQ ID NO: 20 in any combination with a
- variable light chain having a sequence selected from the list of SEQ ID NO: 16, SEQ ID NO: 17, SEQ ID NO: 18, and SEQ ID NO: 19.

B. Antibodies for use according to embodiment A, characterized by a heavy chain corresponding to SEQ ID NO: 1 and a light chain corresponding to SEQ ID NO: 2.

C. Antibodies for use according to embodiment A, characterized by a heavy chain amino acid sequence of SEQ ID NO: 11 and a light chain amino acid sequence of SEQ ID NO: 12.

D. Antibodies for use according to embodiment A, characterized by a heavy chain corresponding to SEQ ID NO: 13 and a light chain corresponding to SEQ ID NO: 14.

E. Antibodies for use according to embodiment A, characterized by a heavy chain corresponding to SEQ ID NO: 21 and a light chain corresponding to SEQ ID NO: 14.

F. Antibodies for use according to embodiment A or C, which are chimeric.

G. Antibodies for use according to embodiment D and E, which are humanized.

H. Antibodies for use according to any of the preceding embodiments, wherein the antibodies are applied at a dose of from 0.25 to 25 mg/kg$_{bodyweight}$.

I Antibodies for use according to embodiment H, wherein the antibodies are applied at a dose of from 1 to 20 mg/kg$_{bodyweight}$.

J. Antibodies for use according to embodiment H, the antibodies are applied at a dose of from 7 to 15 mg/kg$_{bodyweight}$.

K. Antibodies for use according to embodiment H, the antibodies are applied at a dose of from 8 to 12 mg/kg$_{bodyweight}$.

L. A pharmaceutical composition comprising an antibody according to any of the forgoing embodiments A to G alone or in combination with at least one other agent and a pharmaceutically acceptable carrier or excipient, for use in the treatment of CLL in IGLV3-21$^{R110}$ positive patients.

M. A kit comprising a pharmaceutical composition according to embodiment L, for use in the treatment of CLL in IGLV3-21$^{R110}$ positive patients.

DESCRIPTION OF THE FIGURES

FIGS. 1A to 1D show FACS FSC-SSC plots (FIGS. 1A, 1C), as well as the gated plots of mAb01-01-APC (FIGS. 1B, 1D, x-axis) over anti-IgM-PE (FIGS. 1B, 1D, y-axis).

Pursuant to Example 4 the plots in FIGS. 1A and 1B were made from a 1:1 cell mix comprising IGHV3-21/IGLV3-21$^{R110}$ BCR positive TKO mouse cells and TKO cells lacking a BCR (cell mix A) stained with the above fluorescence labelled antibodies, while the plots in FIGS. 1C and 1D were made from a 1:1 cell mix comprising IGHV3-21/IGLV3-21$^{G110}$ BCR positive TKO mouse cells and TKO cells lacking a BCR (cell mix B).

As can be readily appreciated from FIGS. 1B and 1D, nearly the half of the analysed TKO cells are positively stained with the respective anti-IgM antibodies, indicating that they possess a BCR, which is consistent with the expression of the BCR on the surface of approximately 50% of the TKO cells of the respective cell mixes. By virtue of comparison of FIGS. 1B and 1D, it becomes apparent that the antibody of the present invention "mAb01-01" only recognizes the malignant variant of IGLV3-21 bearing the R110 mutation.

FIGS. 2A to 2F show FACS plots of human PBMC's processed pursuant to Example 6. FIGS. 2A and 2D show FSC-SSC representations of said PBMC's in which a gate has been set likewise to FIGS. 1A and 1C to apparently living cells. The gated cells are plotted to have anti-CD19-VioBright515 over anti-CD5-PE-Cy5 (FIGS. 2B and 2E) as well as anti-CD19-VioBright515 over mAb01-01-APC (FIGS. 2C and 2F). FIGS. 2A to 2C depict an analysis of human PBMC's of a patient that was positively diagnosed of having B-cells expressing an IGHV4-39/IGLV3-21$^{R110}$-BCR and FIGS. 2D to 2F depict the same analysis of human PBMC's of a patient whose CLL is not characterized by a IGHV3-21$^{R110}$-BCR (i.e. non-IGLV3-21$^{R110}$ CLL). As can be seen from the comparison of FIGS. 2B and 2D, CD5/CD19$^{++}$ B-cells could be resolved and further comparison between the two patients samples (FIGS. 2C and 2F) shows that mAb01-01 selectively identified IGLV3-21$^{R110}$-positive CLL B-cells only, allowing the differentiation between CLL types.

Figure 3:
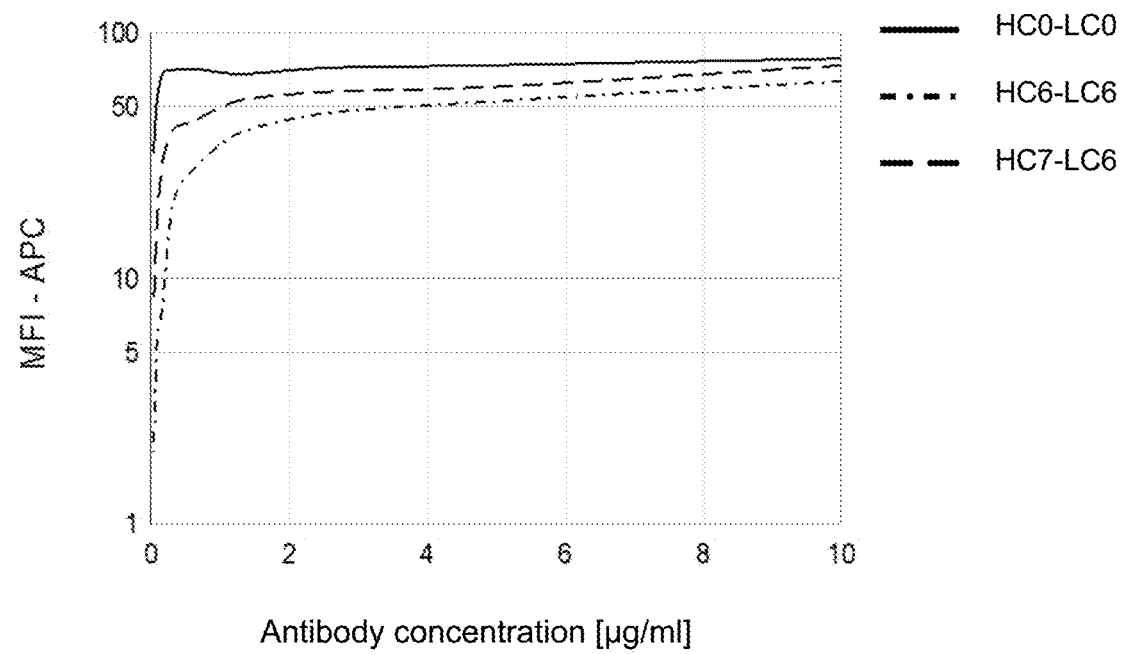

FIG. 3 shows a comparative binding kinetic of the antibodies HC0-LC0, HC6-LC6 and HC7-LC6 pursuant to the present invention and in accordance with Example 7. As can be seen, these three antibodies display essentially the same binding kinetic and have a near to identical binding specificity latest at 10 μg/ml concentration.

Figure 4:
Figure 4:
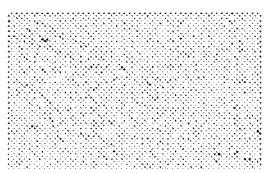
Figure 4:
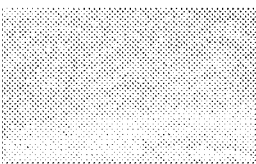
Figure 4:
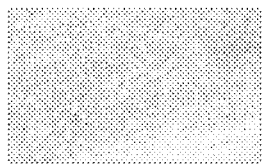
Figure 4:
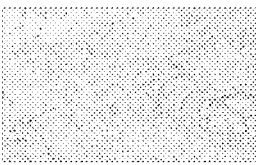
Figure 4:
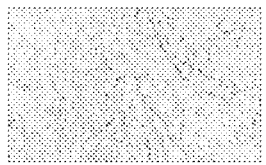
Figure 4:
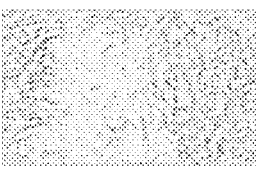
Figure 4:
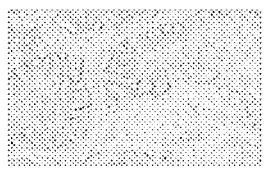
Figure 4:
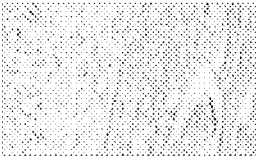
Figure 4:
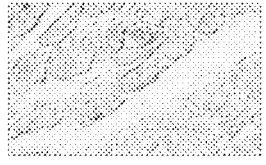
Figure 4:
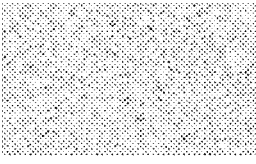
Figure 4:
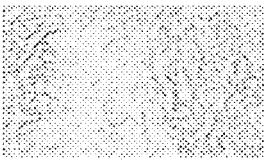

FIG. 4 shows a comparison of (left column) tissues stained with mAb01-01 and an anti-IgG against such mAb01-01 (sandwich-assay) against sole treatment of the same tissue samples solely with anti-IgG (right column) pursuant to Example 8. The top row shows the respective result in a tissue sample of a CLL patient that is IGLV3-21$^{R110}$-positive, while the lower rows show results in healthy donor samples.

From the comparison of the top left picture to all of the remainder pictures of the left column can be seen that the mAb01-01 positively and selectively identifies diseased B-cells in the spleen of a diseased patient and that there is no cross-reactivity to any of the healthy donor's samples neither in the same tissue (spleen), nor in any of the other tissue types (skin, kidney, heart and brain). This shows that the antibodies of the present invention are selective, safe and non-cross-reactive. The further pictures of the right column show that the staining achieved in the top left picture and also the lack of staining in lower pictures of the left column is not related to any background or other artificial effect.

Figure 5:
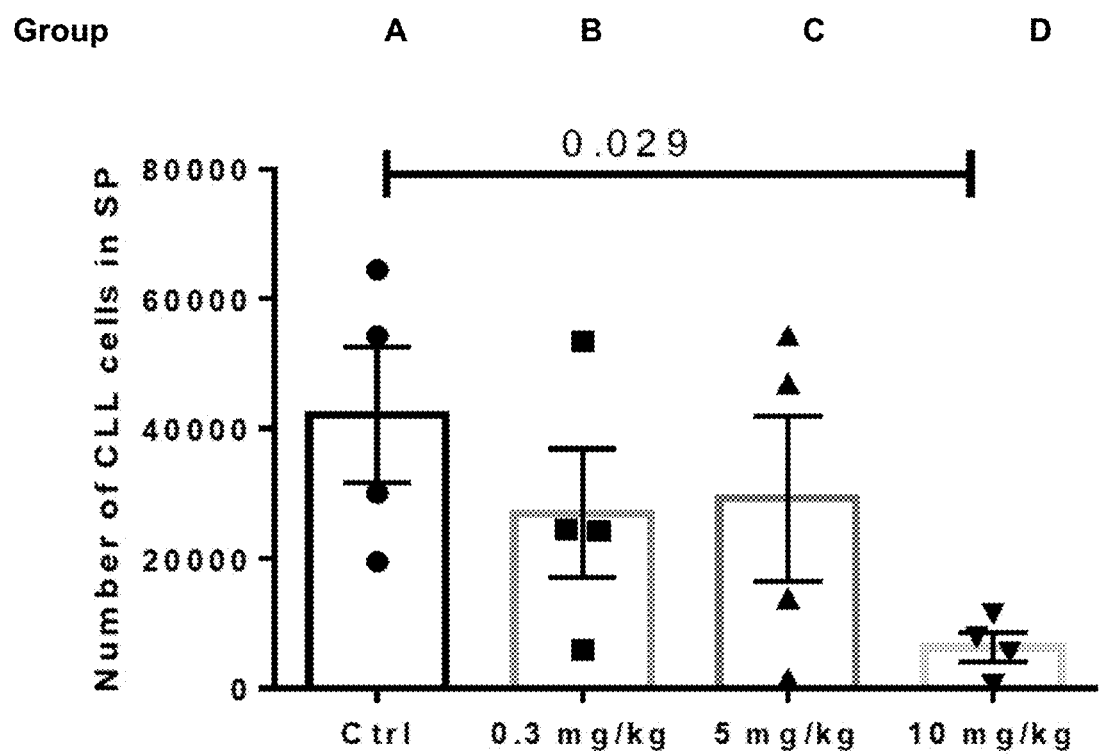

FIG. 5 shows the absolute number of CLL cells in the spleen upon termination of the experiment pursuant to Example 9. In said experiment a xenograft mouse model, artificially suffering from IGLV3-21$^{R110}$-positive CLL was treated with a (pharmaceutically inactive) control (Group A), an amount of 0.3 mg/kg (Group B), an amount of 5 mg/kg (Group C) and 10 mg/kg (Group D) bodyweight of mAb01-01. As can be seen from this figure, all treatments result in a depletion of CLL-cells in the spleen, while at 10 mg/kg the depletion is extraordinary significant. This shows that the antibodies of the present invention indeed facilitate an efficacious treatment of CLL characterized by IGLV3-21$^{R110}$-positive BCRs.

Figures 6, 7, 7A, 7B:
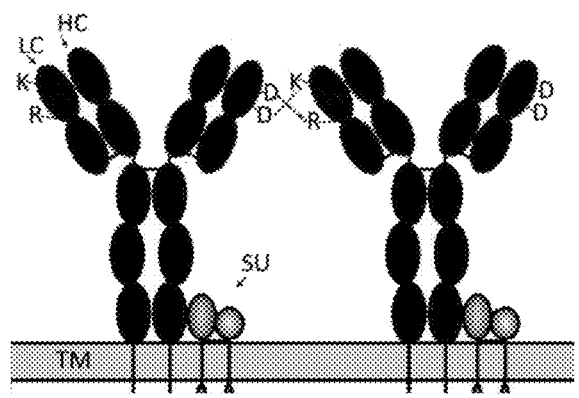

FIG. 6 shows a schematic representation of BCR-BCR homotypic interaction of IGLV3-21$^{R110}$ light chains (as described by Minici et al.). Two neighbouring BCRs are depicted with antigen-binding subunit comprising heavy (HC) and light chains (LC), transmembrane domain (TM), well as the signaling subunit (SU) composed of disulfide-linked heterodimer of the Igα and Igβ proteins (CD79a/CD79b). Mutated arginine at position 110 (R) of one BCR interacts with a germline-encoded aspartate (D) at position 50 of an adjacent BCR. A further interaction between the two BCRs is mediated by the germline-encoded amino acid residues lysine (K) at position 16 and aspartate (D) at position 52.

FIG. 7 shows schematic representations of IGLV3-21$^{R110}$. FIG. 7A: exemplarily IGLV3-21$^{R110}$ (SEQ ID NO: 53) in one-letter code. Amino acid residues involved in BCR-BCR homotypic interactions according to Minici et al. are marked in bold. FIG. 7B: Line 1: Amino acid position in IGLV3-21$^{R110}$. Line 2: Amino acid residues involved in BCR-BCR homotypic interactions according to Minici et al. Line 3: The YDSD-motif. Amino acids are depicted in 3-letter code.

FIG. 8 shows the sequences according to SEQ ID NOs: 1 to 53. SEQ ID NOs: 1-10 show various sequences from the organism *Mus musculus*. SEQ ID NOs: 11-48 show various synthetic construct sequences. SEQ ID NOs: 49-53 show various sequences from the organism *Homo sapiens*.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as de-scribed in standard laboratory manuals, such as Sambrook et al., 1989 supra.

A preferred embodiment of the invention is:

EXAMPLES

Example 1

Generation of Murine Antibodies
Immunization and Generation of Hybridoma Cell Line
A murine antibody to the IGLV3-21$^{R110}$-harboring BCR was developed by a combination of immunization of mice with a soluble form of the BCR and selection of suitable antibodies using a cell system in which the complete and functional BCR was presented membrane bound.

At first, a soluble form of the BCR in the form of an IgG$_1$ had to be obtained for immunization of mice. Therefore, a DNA segment encoding IGHV3-21 as an exemplary variable heavy chain (VH) and a complete light chain (LC) DNA covering IGLV3-21$^{R110}$ were synthesized by a contract manufacturer using a standard procedure. These were then fused with a murine IgG$_1$ constant segment by polymerase chain reaction (PCR) and cloned into a cytomegalovirus (CMV) vector. A human cellular expression system based on HEK293T cells was used for the expression of such IgG$_1$ (SEQ ID NO: 49 for VH, and SEQ ID NO: 50 for LC) as previously described, e.g. in Rekombinante Antikörper, Lehrbuch und Kompendium für Studium und Praxis, 2. Auflage, Springer Verlag 2019. A polyethyleneimine (PEI) based protocol was used for transfection. After several passages, the supernatant was pooled and the medium contained in the combined cell supernatant was purified using Protein G columns. The purity and quality of the soluble IgG$_1$ was determined by Western blotting.

Thereafter, mice were immunized with the recombinantly produced soluble form of the BCR (cf. SEQ ID NOS: 49 and 50).

Immune cells with the desired specificity could then be obtained from these mice and transformed into hybridoma cells by cell fusion. Second, FACS screening methods were performed with triple knockout cells (TKO; knockout for the genes Lambda5, RAG2 and SLP65) expressing various variants for the BCR to select for antibodies specifically targeting BCRs harboring IGLV3-21$^{R110}$.

Monoclonal antibody was produced using the standard procedure in mice and the subsequent generation of hybridoma cells.

This approach allowed the isolation of the unique monoclonal antibody "mAb01-01" (SEQ ID NO: 1 for heavy chain, and SEQ ID NO: 2 for light chain).

Selection of Monoclonal Antibody
The screening for positive clones was not performed by enzyme linked immunosorbent assay (ELISA) as usual. Since the target structure is a membrane-bound receptor, it is of central importance to validate the binding of the potential antibodies in a cellular system, i.e. while largely preserving the cell physiological states native to this cell type. First, groups of pooled supernatants were examined for binding events using fluorescence activated cell sorting (FACS) analysis. For this purpose different BCR variants were expressed on the surface of a triple knockout (TKO) cell line, which cannot express BCR itself.

The starting point for the production of TKO cells is formed by transgenic mice which have a respective knockout for the genes Lambda5, RAG1 or RAG2 and SLP65 (Dühren von Minden et al., 2012, Nature 489, p. 309-313). The combination of the knockouts of RAG2 or RAG1 and Lambda5 leads to a blockade in the transition from the pro-B cell stage to the pre-B cell stage, which is classically characterized by the beginning rearrangement of the VDJ segments of the heavy chain (HC). Therefore they are pro-/pre-B cells. The activity of the BCR can be measured by reconstitution with the inducible SLP65. The production of such mice is known to the expert and belongs to the state of the art. To obtain the cells, the bone marrow of the femur was extracted from the mice after they had been sacrificed. The cells obtained in this way were then cultured under conditions that promote the survival of pro-/pre-B cells (37° C., 7.5% CO2, Iscoves medium, 10% FCS, P/S, murine IL7). After several passages, FACS sorting was carried out for control purposes, the pro-/pre-B cells were sorted and then returned to culture. The markers used for this purpose are known to the specialist.

For reconstitution with a 'BCR of interest', the corresponding sequence coding for the VH was fused with a human IgM constant segment by polymerase chain reaction (PCR), and heavy (HC) and light (LC) chains were cloned into respective expression vectors each having a CMV promoter. These were introduced into the packaging cell line (Phoenix cell line) by lipofection. After 36 hours of incubation, the virus supernatant was removed and used for Spinfektion of the TKO cells. BCR expression was determined using anti-IgM and anti-LC antibodies on FACS. For this purpose, some cells were taken and stained with 5 µl antibody each in a total volume of 100 µl in PBS. Both the work to extract the supernatants and the Spinfektion of the TKO are widely known procedures and known to experts. Knockout of RAG2 or RAG1 and Lambda5 ensured that only the "BCR of Interest" was expressed on the surface.

In this way, two different BCR-expressing TKO cell lines were generated, one of which expressed the membrane-bound IGHV3-21/IGLV3-21$^{R110}$ BCR. For the generation of the second BCR-expressing TKO cell line, the codon for the arginine at position 110 of the DNA encoding IGLV3-21$^{R110}$ was reverted to the germline sequence by well-known site-directed mutagenesis technique (see, e.g. Sambrook et al., 1989 supra). The resulting TKO cells expressed a BCR containing IGLV3-21 with glycine at amino acid position 110)(IGLV3-21$^{G110}$). To generate a third control TKO cell line without BCR expression on its surface, spinfection with an empty expression vector was performed. By using an inducible SLP65 to reconstitute the cells, the function of the expressed BCRs could be characterized and the autonomously active state of the IGHV3-21/IGLV3-21$^{R110}$ BCR on the surface could thus be verified before selection. The method of choice here is the measurement of Ca-flux after induction of SLP65 using FACS analysis and the use of a Ca$^{2+}$ dependent dye such as Indo-1. These methods are known to the expert (see M. Dühren-von Minden et. al; Nature 2012).With these cells as "targets", FACS has now been used to identify an antibody that specifically binds to IGLV3-21$^{R110}$-harboring BCRs. The first step was to identify the supernatants whose antibodies showed a binding. In this 1st selection round, supernatants of several clones were combined and examined with regard to their binding profile. A positive binding profile is given if a specific binding to the IGHV3-21/IGLV3-21$^{R110}$-BCR is shown. Groups showing such a profile were isolated, and the binding profile of the individual clones was characterized again during a second selection round. Binding of the monoclonal antibodies was verified using a FACS binding assay using a fluorescently labeled anti-mouse IgG antibody.

This selection approach led to the identification of the antibody mAb01-01, which binds the IGHV3-21/IGLV3-21$^{R110}$ BCR positive TKO mouse cells, but not IGHV3-21/IGLV3-21$^{G110}$ BCR positive TKO mouse cells.

Production of Murine Antibody

After identification of a preferred antibody by selection, mRNA was isolated from the individual hybridoma clone, cDNA was generated and amplified by Anchor PCR (Rapid expression cloning of human immunoglobulin Fab fragments for the analysis of antigen specificity of B cell lymphomas and anti-idiotype lymphoma vaccination; Osterroth F, Alkan O, Mackensen A, Lindemann A, Fisch P, Skerra A, Veelken H. J Immunol Methods 1999 Oct. 29; 229(1-2):141-53). The sequence of the cDNA encoding the monoclonal antibody mAb01-01 was confirmed by Sanger sequencing (SEQ ID NO: 25 for HC nucleotide, SEQ ID NO: 26 for LC nucleotide) and placed into a vector suitable for expression in CHO cells.

Expression of the mAb01-01 as IgG1 subtype was verified using secondary anti-murine IgG1-APC and IgG2-APC antibodies. For this purpose, IGHV3-21/IGLV3-21$^{R110}$-expressing TKO cells were stained in one batch with the secondary antibody alone and in another batch with mAb01-01 and the secondary antibody. Subsequent FACS analysis confirmed that the antibody had been expressed as IgG1.

The specific monoclonal antibody mAb01-01 was sequenced. The following amino acid sequences were determined as depicted in Table 1: SEQ ID NO: 1 for the HC, SEQ ID NO: 2 for the LC, SEQ ID NO: 3 for the VH, SEQ ID NO: 4 for the VL. The sequences corresponding to complementarity determining regions (CDR) of the heavy chain, H-CDR1, H-CDR2 and H-CDR3 are included in SEQ ID NOS: 5, 6 and 7, while the sequences corresponding to the light chain CDRs, L-CDR1, L-CDR2 and L-CDR3 are included in SEQ ID NOS: 8, 9 and 10.

Example 2

Generation of Chimeric Antibodies

Using the murine monoclonal antibody mAb01-01 VH and VL nucleotide sequences (SEQ ID NO: 27 for VH Nucleotide, and SEQ ID NO: 28 for VL Nucleotide) a chimeric antibody was synthesized. For this purpose, the VH sequence was fused with a human IgG1 isotype constant domain sequence (SEQ ID NO: 31 for IgG1 constant Nucleotide) and the VL sequence was fused with a human IgK isotype constant domain (SEQ ID NO: 32 for IgK constant Nucleotide) by PCR and expressed using a CHO based transient expression system. The resulting antibody containing cell culture supernatant was clarified by centrifugation and filtration. The chimeric antibody was purified from cell culture supernatant via affinity chromatography. The purity of the antibody was determined to be >95%, as judged by reducing and denaturing Sodium Dodecyl Sulfate Polyacrylamide Gel Electrophoresis (SDS-PAGE). The antibody was analyzed for protein content and concentration via Seize Exclusion Chromatography (SEC) in PBS-buffer. All steps were performed with state-of the-art equipment and techniques.

This approach resulted in the chimeric antibody "HC0-LC0", the sequences of which are summarized in Table 1.

TABLE 1

Sequences of murine and chimeric antibodies

| Antibody | SEQ ID NO: HCDR1 | SEQ ID NO: HCDR2 | SEQ ID NO: HCDR3 | SEQ ID NO: LCDR1 | SEQ ID NO: LCDR2 | SEQ ID NO: LCDR3 | SEQ ID NO: VH Protein | SEQ ID NO: VL Protein | SEQ ID NO: HC Protein |
|---|---|---|---|---|---|---|---|---|---|
| mAb01-01 | 5 | 6 | 7 | 8 | 9 | 10 | 3 | 4 | 1 |
| HC0-LC0 | 5 | 6 | 7 | 8 | 9 | 10 | 3 | 4 | 11 |

| Antibody | SEQ ID NO: LC Protein | SEQ ID NO: VH Nucleotide | SEQ ID NO: VL Nucleotide | SEQ ID NO: HC Nucleotide | SEQ ID NO: LC Nucleotide | SEQ ID NO: HC + LC Protein |
|---|---|---|---|---|---|---|
| mAb01-01 | 2 | 27 | 28 | 25 | 26 | 39 |
| HC0-LC0 | 12 | 27 | 28 | 29 | 30 | 40 |

Example 3

Generation of Humanized Antibodies

Humanization of mAb01-01 was carried out by in silico grafting the murine CDR's into mature human antibody frameworks using standard CDR-grafting technologies by Fusion Antibodies Plc, Belfast, N. Ireland. Key residues important for the VH/VL interface and canonical loop structure have been maintained as much as possible in the humanized variants using the CDRx platform (Fusion Antibodies Plc, Belfast, N. Ireland). Subsequently, the amino acid sequences of the humanized variants generated by fusion antibodies were converted to nucleotide sequences using Geneiouse software (Geneious Prime 2, Auckland, New Zealand). By fusing VH sequences with a human IgG1 isotype constant domain sequence (SEQ ID NO: 31 for IgG1 constant Nucleotide) and VL sequences with a human IgK isotype constant domain (SEQ ID NO: 32 for IgK constant Nucleotide) by PCR, 16 pairs of the humanized heavy and light chains were generated, and the antibody gene sequences expressed transiently in Chinese Hamster ovary cells (CHO). Following batch culture, expressed humanized antibodies were purified from the cell culture supernatant and analyzed as described in Example 2 for HC0-LC0. Eight humanized antibodies as depicted in Table 2 were successfully yielded.

μg/ml mAb01-01-APC, 2 μg/ml Anti-human IgM-PE, in a total volume of 100 μl) in PBS buffer, and incubated for 15 min at 4° C. in the dark. In the following, cells were washed once with 1 ml cold PBS buffer, resuspended in 200 μL cold PBS buffer.

FACS analysis was performed by using a MACSQUANT® Analyzer 10 (Miltenyi Biotec B.V. & Co. KG; the instrument was calibrated as recommended by the manufacturer, flow rate: Low, Mix sample: Mix gentle, Mode, Standard, Uptake volume: 50 μL, Sample volume: 200 μL). TKO-cells of cell mix A or cell mix B were gated in a side scatter (SSC) vs. forward scatter (FSC) and the gated TKO-cells were analysed in anti-IgM-PE vs. mAb01-01-APC dot-plot to enumerate the different TKO-cell populations using quadrant stats.

As shown in FIGS. 1A to 1D, mAb01-01 binds to murine TKO cells expressing human IGLV3-21$^{R110}$-BCR, whereas no binding occurs to human IGLV3-21$^{G110}$-BCR expressing TKO mouse cells.

Example 5

Affinity of Antibodies for the IGLV3-21$^{R110}$ B-Cell Receptor

To define the binding affinities of the antibodies to the IGLV3-21$^{R110}$-harboring B-cell receptor, a soluble recom-

TABLE 2

Sequences of humanized antibodies

| Antibody | SEQ ID NO: HCDR1 | SEQ ID NO: HCDR2 | SEQ ID NO: HCDR3 | SEQ ID NO: LCDR1 | SEQ ID NO: LCDR2 | SEQ ID NO: LCDR3 | SEQ ID NO: VH Protein | SEQ ID NO: VL Protein | SEQ ID NO: HC Protein | SEQ ID NO: LC Protein | SEQ ID NO: VH Nucleotide | SEQ ID NO: VL Nucleotide | SEQ ID NO: HC + LC Protein |
|---|---|---|---|---|---|---|---|---|---|---|---|---|---|
| HC6-LC6 | 5 | 6 | 7 | 8 | 9 | 10 | 15 | 16 | 13 | 14 | 33 | 34 | 41 |
| HC6-LC7 | 5 | 6 | 7 | 8 | 9 | 10 | 15 | 17 | 13 | 22 | 33 | 35 | 42 |
| HC6-LC8 | 5 | 6 | 7 | 8 | 9 | 10 | 15 | 18 | 13 | 23 | 33 | 36 | 43 |
| HC6-LC9 | 5 | 6 | 7 | 8 | 9 | 10 | 15 | 19 | 13 | 24 | 33 | 37 | 44 |
| HC7-LC6 | 5 | 6 | 7 | 8 | 9 | 10 | 20 | 16 | 21 | 14 | 38 | 34 | 45 |
| HC7-LC7 | 5 | 6 | 7 | 8 | 9 | 10 | 20 | 17 | 21 | 22 | 38 | 35 | 46 |
| HC7-LC8 | 5 | 6 | 7 | 8 | 9 | 10 | 20 | 18 | 21 | 23 | 38 | 36 | 47 |
| HC7-LC9 | 5 | 6 | 7 | 8 | 9 | 10 | 20 | 19 | 21 | 24 | 38 | 37 | 48 |

Example 4

Binding of mAb01-01 to IGLV3-21$^{R110}$-BCR and IGLV3-21$^{G110}$-BCR expressing TKO Cells The specificity of the antibody mAb01-01 observed in the selection (Example 1) was verified in a FACS assay using the antibody coupled to a fluorescent marker.

For this purpose, from the three different TKO cell lines according to Example 1 two cell mixtures, cell mix A and cell mix B, were prepared and subsequently stained with mAb01-01-APC (mAb01-01 was coupled with fluorescent marker APC by Immunotools GmbH). For control, each batch was additionally stained with anti-IgM antibody (Anti-human IgM-PE, Clone: MHM-88, BioLegend Cat-No.: 314508).

Cell mix A was prepared at a 1:1 ratio of IGHV3-21/IGLV3-21$^{R110}$ B-cell receptor expressing TKO cells and B-cell receptor negative (empty vector; control) TKO cells in PBS buffer (Gibco, pH 7.2, Cat. no. 20012-019).

Cell mix B was prepared at a 1:1 ratio of IGHV3-21/IGLV3-21$^{G110}$ B-cell receptor expressing TKO cells and B-cell receptor negative (empty vector; control) TKO cells in PBS buffer.

Cells of cell mix A or B were suspended at approximately 10$^6$ cells per FACS tube in dilutions of the antibodies (5 binant version of the BCR (170.5 kDa; sequence according to SEQ ID NO: 51 for HC and 52 for LC) was produced in 293-HEK cell line as monomeric human IgM by transient expression using a protocol described in Example 1, and binding to immobilized anti-IGLV3-21$^{R110}$ antibodies was monitored by Bio-Layer Interferometry (BLI) on a Fortebio Octet instrument (Satorius).

Kinetic assays were performed by first immobilizing the anti IGLV3-21$^{R110}$ antibodies onto biosensors through an indirect capturing reagent, anti-human IgG Fc antibody. Anti IGLV3-21$^{R110}$ antibodies were loaded at a concentration of 0.01875 μg/ml to generate an anti IGLV3-21$^{R110}$ antibody capture level of between 0.30 and 0.34 nm. A 9 nM BCR-fragment solution in running buffer (PBS, 0.02% TWEEN® 20 (Polyethylene glycol sorbitan monolaurate), 0.1% BSA, 0.05% sodium acide) was prepared and serial diluted 1:3 to obtain 7 concentrations from 9 to 0.012 nM (9 nM, 3 nM, 1 nM, 0.333 nM, 0.111 nM, 0.037 nM, and 0.012 nM). The anti IGLV3-21$^{R110}$ antibody capture biosensors were then submerged in wells containing the different concentrations of the soluble BCR-fragment for 900 seconds (association stage) followed by a dissociation step of 1200 seconds in running buffer. Steps were performed at a constant shake speed of 1000 rpm. All reagents were used as described by the manufacturer. Sensorgrams were generated after double reference correction (buffer and blank sensors) to compensate for both the natural dissociation of the capture anti IGLV3-21$^{R110}$ antibody and also non-specific binding of the soluble BCR-fragment to the sensor surface. Dissociation rate constants (KD) were calculated based on the ratio of association (ka) and dissociation rate (kd) constants, obtained by fitting sensorgrams with a first order 1:1 binding model using the Fortebio Data Analysis software (Satorius).

As shown in Table 3, chimeric antibody HC0-LC0 binds with a $K_D$ value around 120 nM the soluble IGLV3-21$^{R110}$ B-cell receptor. The humanized antibodies HC6-LC6 and HC7-LC6 exhibit binding characteristics similar to that of chimeric antibody HC0-LC0, exhibiting dissociation constants within 2-fold of the chimeric antibody HC01 LC01. For the $K_D$ values of all humanized antibodies, see Table 3.

TABLE 3

Monovalent $K_D$ values of chimeric antibody HC0-LC0 and humanized variants as measured by Fortebio with soluble IGLV3-21$^{R110}$ B-cell receptor and anti IGLV3-21$^{R110}$ antibody Capture levels

| Antibody | $K_D$ (M) | Capture level (nm) |
| --- | --- | --- |
| HC0-LC0 | 1.21E−10 | 0.322 |
| HC6-LC6 | 2.11E−10 | 0.305 |
| HC6-LC7 | 3.47E−10 | 0.337 |
| HC6-LC8 | 2.77E−10 | 0.313 |
| HC6-LC9 | 2.91E−10 | 0.311 |
| HC7-LC6 | 1.75E−10 | 0.322 |
| HC7-LC7 | 2.69E−10 | 0.323 |
| HC7-LC8 | 2.49E−10 | 0.330 |
| HC7-LC9 | 3.13E−10 | 0.280 |

Example 6

Binding of Murine Antibody mAb01-01 to Cell Surface of IGLV3-21$^{R110}$-BCR Positive Human B-CLL Cells To determine the binding characteristics of the mAb01-01 on IGLV3-21$^{R110}$-B-cell receptor positive human CLL cells vs. non-IGLV3-21$^{R110}$ human B-cells, binding was tested by flow cytometry.

For this purpose, cryopreserved peripheral blood mononuclear cells (PBMCs) of two CLL patients were used. The CLL in one of these patients was characterized by the presence of IGLV3-21$^{R110}$. More specifically, the CLL cells expressed a BCR with a combination of IGLV3-21$^{R110}$ with IGHV4-39 heavy chain (IGHV4-39/IGLV3-21$^{R110}$-BCR). The other patient had been diagnosed suffering with a non-IGLV3-21$^{R110}$ CLL. The PBMCs could be separated from heparinized venous blood by Ficoll-Paque PLUS (GE Healthcare Bio-Sciences AB) density gradient centrifugation using a technique that is known in the art, e.g. according to Bøyum A. Isolation of mononuclear cells and granulocytes from human blood. Scan. J. Clin. Lab. Invest. 1968, 21 (Suppl. 97): 77-89.

Samples where thawed and resuspended in 5 ml cell culture medium (RPMI, Gibco; 10% FCS, PAN-Biotec). Cells were centrifuged by 300 g (Eppendorf centrifuge 5425R), followed by additional resuspension in 1 ml RPM I. Cell count was acquired by using a Neubauer Chamber. For staining 1×10E6 cells were used and transferred in a FACS-tube. Cells were stained using 2 µl anti-CD19 Vio-Bright515 (Miltiny Biotech, Klon:REA675), 2 µl Anti-CD5-PE-Vio770 (Miltenyi Biotec, Klon:REA782), and 5 µl mAb01-01-APC (mAb01-01 was coupled with fluorescent markers APC by Immunotools GmbH) in a total volume of 100 µl PBS buffer, and incubated for 15 min at 4° C. in the dark. In the following, cells were washed once with 1 ml cold PBS buffer, resuspended in 200 µL cold PBS buffer and analysed by flow cytometry using a BD LSRFortessa™ Cell Analyzer (BDbioscience). The instrument was calibrated as recommended by the manufacturer. The Analysis of the raw data were performed by using the FlowJo-Software X (BD-bioscience). The analysis gates where set as demonstrated in FIG. 2.

As shown in FIG. 2, the mAb01-01 binds exclusively to IGLV3-21$^{R110}$ positive CLL B cells, but not to BCRs of a CLL patient, which does not harbor IGLV3-21$^{R110}$. More specifically, mAb01-01 recognizes the IGLV3-21$^{R110}$-BCR irrespective of the nature of the heavy chain.

Example 7

Binding Characteristics of Chimeric and Humanized Antibodies to Cell Surface of IGLV3-21$^{R110}$-BCR Positive Murine TKO Cells To compare the specific IGLV3-21$^{R110}$-BCR binding of the chimeric antibody and two humanized versions, IGLV3-21$^{R110}$-BCR murine TKO cells (see Example 1) were incubated with different concentrations of the antibodies HC0-LC0, HC6-LC6 and HC7-LC6 and analysed by flow cytometry and a sandwich assay setup. Controls were performed with a TKO—empty vector cell line (without surface BCR).

From each cell line, 7.5×10E6 cells are transferred into a separate 15 ml bluecap, centrifuged for 10 minutes (300 g, at 4° C.), and resuspended in 1.5 ml PBS (Gibco).

Staining where performed in a 96-well plate (VWR, U-bottom, non-treated). For each reaction 2×10E5 cells were used. The experimental setup is shown in Table 4.

TABLE 4

Experimental setup of the 96-well plate

| | well No./Conc. (µg/ml) | | | | | | | | | | |
| --- | --- | --- | --- | --- | --- | --- | --- | --- | --- | --- | --- |
| | 1 | 2 | 3 | 4 | 5 | 6 | 7 | 8 | 9 | 10 | 1st Ab |
| A: TKO-R110 | 10.00 | 5.00 | 2.50 | 1.25 | 0.63 | 0.31 | 0.16 | 0.08 | 0.04 | 0.00 | HC0/LC0 |
| B: TKD-emty vector | 10.00 | 5.00 | 2.50 | 1.25 | 0.63 | 0.31 | 0.16 | 0.08 | 0.04 | 0.00 | HC0/LC0 |
| C: TKO-R110 | 10.00 | 5.00 | 2.50 | 1.25 | 0.63 | 0.31 | 0.16 | 0.08 | 0.00 | 0.00 | HC7/LC6 |
| D: TKO empty vector | 10.00 | 5.00 | 2.50 | 1.25 | 0.63 | 0.31 | 0.16 | 0.08 | 0.04 | 0.00 | HC7/LC6 |
| C: TKO R110 | 10.00 | 5.00 | 2.50 | 1.25 | 0.63 | 0.31 | 0.16 | 0.08 | 0.04 | 0.00 | HC6/LC6 |
| D: TKO-empty vector | 10.00 | 5.00 | 2.50 | 1.25 | 0.63 | 0.31 | 0.16 | 0.08 | 0.04 | 0.00 | HC6/LC6 |

To characterize the binding characteristics of the different humanized variants 10 different concentrations of each antibody in PBS were used for staining (10, 5, 2.5, 0.625, 0.31, 0.16, 0.08, 0.04, 0 µg/ml) in a total volume of 200 µl per well. Incubation was performed for 30 min at 4° C., dark. The 96-well was then centrifuged (VWR, MEGA STAR 1.6R) for 10 min at 300 g, 4° C. Supernatants were discarded and the cells were resuspended in 100 µl ice cold PBS. For detection a secondary antibody directed to human IgG1 labeled with APC was used in a final concentration of µg/ml.

Incubation was performed in 200 µl/well total volume for 15 min at 4° C. in the dark, followed by an additional washing step with ice cold PBS. Cells were resuspended in 150 µl ice cold PBS for acquisition. Cells were analysed on a MACS-Quant10 (Miltenyi Biotec), calibrated followed by the instruction of the manufacturer.

MFI (median fluorescence intensity) of all IGLV3-21$^{R110}$-BCR TKO measurements was neutralized by subtracting the control cell values and plotted against the concentration of the antibodies. Functions were generated demonstrating a concentration-dependent increase in binding of the IGLV3-21$^{R110}$-BCR for all three antibodies. As shown in FIG. 3, the two humanized variants exhibit increasingly identical binding properties to the chimeric antibody with increasing antibody concentration and have nearly identical binding specificities at 10 µg/ml at the latest.

Example 8

Tissue Cross-Reactivity Profile of mAb01-01

To determine the binding characteristics of mAB01-01 to human CLL and healthy tissue in immunohistochemistry (IHC) experiments, immunostaining was performed on sections of spleen tissue expressing the IGLV3-21$^{R110}$-BCR and of healthy spleen, skin, kidney, heart, and brain tissue.

Prior to IHC, the tissue sections were deparaffinized and hydrated. To unmask the antigens, microwave treatment with citrate buffer pH 6.0 (9 ml citric acid (0.1M) and 41 ml sodium citrate (0.1 M)) was performed. For this, the sections were boiled in the bubbling citrate buffer for 15 min, after which they chilled at room temperature for 30 min and then they were rinsed in PBS 3×5 min. For IHC, the slides were incubated for 2 hr with the first antibody at a dilution of 1:200 at RT in a humidity chamber. As a control, sections of all tissues were incubated under identical conditions without the first antibody. Thereafter, the slides were washed in PBS 3×5 min. An anti-IgG antibody conjugated with horseradish peroxidase (HRP) (Goat Anti-Mouse IgG(H+L)-HRP, Southern Biotech, Cat. No. 1036-05) as a secondary antibody was incubated for 1 hour at a dilution of 1:10000 at RT in a humidified chamber. Subsequently, it was washed with PBS for 10 min and a DAB substrate kit (#34065, Thermo Fisher) was used to detect the activity of the HRP. DAB (3,3'-Diaminobenzidine tetrahydrochloride) substrate was incubated for 15 min. Fluoromount-1 was used as the capping agent. The evaluation was done after 30 minutes and showed an insoluble, brown colored reaction product at the sites where HRP conjugated anti-IgG antibody bound to the tissue.

As shown in FIG. 4, positive staining could be observed for the IGLV3-21$^{R110}$-BCR positive spleen section, thus mAb01-01 is cross-reactive in binding to human CLL-tissue. In contrast, no staining was detected in healthy human tissue sections of spleen, skin, kidney, heart, and brain. Thus mAB01-01 shows no cross-reactivity with healthy human tissue.

Example 9

Test of Anti-IGLV3-21$^{R110}$-BCR Antibodies in a Patient Derived Xenograft Model To determine the efficacy of the anti-IGLV3-21$^{R110}$ antibodies a patient derived xenograft model was chosen. For a Dose finding experiment 4 groups with 4 NOD-scid IL2rg null (NSG)-mice (Jackson ImmunoResearch, prepared as described in Qi J et al.: An IgG1-like bispecific antibody targeting CD52 and CD20 for the treatment of B-cell malignancies, Methods 2019, 154:70-76) were used:
Group A: control group without antibody treatment
Group B: dose 0.3 mg/kg body weight
Group C: dose 5 mg/kg body weight
Group D: dose 10 mg/kg body weight PMBS from an IGLV3-21$^{R110}$-BCR patient were thawed and resuspended in PBS. T cells where separated by using Miltenyi CD3 Beads (Miltenyi Biotec) following the instruction for use provided by the manufacturer. T cells were cultured and expanded for 7 days using CD3/CD28 dynabeads (Dynabeads™ Human T-Activator CD3/CD28 for T Cell Expansion and Activation, Cat. No. 11161D, GIBCO) as described before (Qi J et al. Methods, 2019 s.a.).

After 7 days, the activated T cells and PBMCs (20×10$^6$ CLL PBMCs and 5×10$^5$ T cells per mouse) were injected i.v. into NSG mice. For treatment mAb01-01 was given in different dosages i.p., twice a week for total 3 weeks, starting at week 2 post engraftment. Mice where pre-conditioned at the beginning of every week with 250 µl human serum. The mice were sacrificed after 3 weeks of treatment. For analysis the spleen was isolated and analyzed for the existence of human IGLV3-21$^{R110}$ positive CLL B cells by flow cytometry using the mAb01-01 and antibodies against human CD45, CD5S, and CD19 (CD5 IgG1 UCHT2, BioLegend; CD19 IgG1 HIB19, BD Biosciences; CD45 (human) IgG1 H130 Invitrogen). For flow cytometry, cells were collected by centrifugation and resuspended in ice-cold 0.1% (w/v) BSA in PBS (flow cytometrybuffer). 100 µL containing 5×10$^5$ cells were distributed into a V-bottom 96-well plate (Corning). The cells were first blocked with 5% (v/v) goat serum (Jackson ImmunoResearch) for 30 min on ice and then incubated with the indicated antibodies as recommended by the manufacturer. The cells were incubated for 30 min on ice in dark. Then the cells were washed twice with ice-cold flow cytometry buffer, resuspended in 200 µL flow cytometry buffer and analyzed using FACSCanto (BD Biosciences).

As shown in FIG. 5, the treatment with mAb01-01 led to a reduction in tumor cell counts in all treated mice, and treatment with 10 mg/kg mAb01-01 reduced tumor growth supremely.

The invention claimed is:

1. A monoclonal antibody that specifically binds to IGLV3-21$^{R110}$-harboring B-cell receptor (BCR) comprising a heavy chain and a light chain, comprising
   (a) the heavy chain amino acid sequence of SEQ ID NO: 1 and the light chain amino acid sequence of SEQ ID NO: 2; or
   (b) the heavy chain amino acid sequence of SEQ ID NO: 11 and the light chain amino acid sequence of SEQ ID NO: 12; or
comprising
   (c) a variable heavy chain having a sequence selected from the list consisting of SEQ ID NO: 15 and SEQ ID NO: 20 in any combination with a variable light chain having a sequence selected from the list consisting of SEQ ID NO: 16, SEQ ID NO: 17, SEQ ID NO: 18, and SEQ ID NO: 19.

2. The monoclonal antibody according to claim 1, wherein the heavy chain comprises SEQ ID NO: 1 and the light chain comprises SEQ ID NO: 2.

3. The monoclonal antibody according to claim 1, wherein the heavy chain amino acid sequence comprises SEQ ID NO: 11 and the light chain amino acid sequence comprises SEQ ID NO: 12.

4. The monoclonal antibody according to claim 1, wherein the heavy chain comprises SEQ ID NO: 13 and the light chain comprises SEQ ID NO: 14.

5. The monoclonal antibody according to claim 1, wherein the heavy chain comprises SEQ ID NO: 21 and the light chain comprises SEQ ID NO: 14.

6. The monoclonal antibody according to claim 1, wherein said monoclonal antibody is chimeric.

7. The monoclonal antibody according to claim 1, wherein said monoclonal antibody is humanized.

8. A pharmaceutical composition comprising said monoclonal antibody according to claim 1 and a pharmaceutically acceptable carrier or a pharmaceutically acceptable excipient.

9. A kit comprising the pharmaceutical composition according to claim 8.

10. The pharmaceutical composition of claim 8, wherein the pharmaceutical composition is formulated to be applied at a dose of said monoclonal antibody from 0.25 to 25 mg/kg$_{bodyweight}$.

11. The pharmaceutical composition of claim 8, wherein the heavy chain of said monoclonal antibody comprises SEQ ID NO: 13, the light chain of said monoclonal antibody comprises SEQ ID NO: 14 and the pharmaceutical composition is formulated to be applied at a dose of said monoclonal antibody from 0.25 to 25 mg/kg$_{bodyweight}$.

12. The pharmaceutical composition of claim 8, wherein the heavy chain of said monoclonal antibody comprises SEQ ID NO: 21 and the light chain of said monoclonal antibody comprises SEQ ID NO: 14 and the pharmaceutical composition is formulated to be applied at a dose of said monoclonal antibody from 0.25 to 25 mg/kg$_{bodyweight}$.

* * * * *